US008241371B2

(12) United States Patent
Hanna et al.

(10) Patent No.: US 8,241,371 B2
(45) Date of Patent: Aug. 14, 2012

(54) METHOD OF CREATING CRYSTALLINE SUBSTANCES

(75) Inventors: Mazen Hanna, Bradford (GB); George Townend, West Yorkshire (GB)

(73) Assignee: Thar Pharmaceuticals, Inc., Pittsburgh, PA (US)

( * ) Notice: Subject to any disclaimer, the term of this patent is extended or adjusted under 35 U.S.C. 154(b) by 938 days.

(21) Appl. No.: 12/027,883

(22) Filed: Feb. 7, 2008

(65) Prior Publication Data

US 2008/0280858 A1    Nov. 13, 2008

(30) Foreign Application Priority Data

Feb. 8, 2007 (GB) .................................. 0702402.9

(51) Int. Cl.
*B01D 9/00* (2006.01)
(52) U.S. Cl. ........................................ 23/300; 23/295 R
(58) Field of Classification Search ................ 23/295 R, 23/300
See application file for complete search history.

(56) References Cited

U.S. PATENT DOCUMENTS

| 6,620,351 | B2 | 9/2003 | Gupta et al. | |
| 7,150,766 | B2 * | 12/2006 | Hanna et al. .................... | 23/300 |
| 2005/0267209 | A1 | 12/2005 | Peterson et al. | |
| 2007/0026078 | A1 * | 2/2007 | Almarsson et al. ........... | 424/489 |

FOREIGN PATENT DOCUMENTS

| WO | 9501221 | A1 | 1/1995 |
| WO | 9600610 | A1 | 1/1996 |
| WO | 9817676 | A1 | 4/1998 |
| WO | 9959710 | A1 | 11/1999 |
| WO | 0103821 | A1 | 1/2001 |
| WO | 0115664 | A2 | 3/2001 |
| WO | 03008082 | A1 | 1/2003 |
| WO | 2004062785 | A1 | 7/2004 |
| WO | 2005089375 | A2 | 9/2005 |
| WO | 2005105293 | A1 | 11/2005 |

OTHER PUBLICATIONS

GB Search Report for Application No. GB0702402.9 dated Jun. 18, 2007, 1 page.
International Search Report for PCT/GB2008/000429, dated Jun. 5, 2008. 5 pages.
Callahan et al., "Equilibrium Moisture Content of Pharmaceutical Excipents", Drug Development and Industrial Pharmacy, 1982, pp. 355-369, vol. 8, No. 3.
Shan et al., "Mechanochemistry and co-crystal formation: effect of solvent on reaction kinetics", Chemical Communication, 2002, pp. 2372-2373, No. 20.
Subramaniam et al., "Pharmaceutical Processing with Supercritical Carbon Dioxide", Journal of Pharmaceutical Sciences, pp. 885-890, 1997, vol. 86, No. 8.
Ventosa et al., "DELOS process: a cytstallization technique using compressed fluids 1. Comparison to the GAS crystallization method", Journal of Supercritical Fluids, 2003, pp. 33-45, vol. 26, Issue 1.
Tom et al., "Particle Formation with Supercritical Fluids, A Review", Journal of Aerosal Science, 1991, pp. 555-584, vol. 22, No. 5.
Chattopadhyay et al., "New Enabling Technologies for Drug Delivery", Drug Delivery Technology, 2006, pp. 64-68, vol. 5, No. 8.
Third Party Observations Against European Application No. 08709339.9, dated Mar. 21, 2012, 18 pgs.
Juppo et al., "Evaluation of solid dispersion particles prepared with SEDS", International Journal of Pharmaceutics, 2003, pp. 385-401, vol. 250.
Sethia et al., "Physicochemical Characterization of Solid Dispersions of Carbamazepine Formulated by Supercritical Carbon Dioxide and Conventional Solvent Evaporation Method", J Pharm Sci, 2002, pp. 1948-1957, vol. 91, No. 9.
Werling et al., "Numerical modeling of mass transfer in the supercritical antisolvent process", J Supercritical Fluids, 1999, pp. 167-181, vol. 16.
Baldyga et al., "Supercritical fluid technology for drug development", Drugs and Pharm Sci, vol. 138, Chapter 3, p. 110, Figure 7.

* cited by examiner

*Primary Examiner* — Edward Johnson

(57) ABSTRACT

Process for preparing a cocrystal of an active substance and a cocrystal former, the process involving precipitating the active substance and the cocrystal former together from solution or suspension, in the presence of a supercritical or near-critical fluid, in particular using a GAS, SAS, SEDS or SAS-EM process. The invention also provides a cocrystal prepared using such a process, and its use as a seed crystal in a subsequent process for precipitating a cocrystal of an active substance and a cocrystal former.

25 Claims, 17 Drawing Sheets

Key to Figure (1)

| Item | Description | Item | Description |
|---|---|---|---|
| A | Liquefied Carbon Dioxide Cylinder | K | Heated Jacket (Formation Vessel) |
| B | Drug Solution Container | L | Particle Formation Vessel |
| C | Drug Solution Pump | M | Mass Flow Meters |
| D | Carbon Dioxide Pump | N | Particle Retention Device (Filter) |
| E | Solution Heat Exchanger | P | Pressure Gauge / Pressure Transducer |
| F | Carbon Dioxide Heat Exchanger | Q | Automated Back Pressure Regulator |
| G | Carbon Dioxide Sub-Cooler | R | Vent Line Heat Exchanger |
| H | Piezo-Electric Ultrasonic Cell | S | Solvent Separation / Collection System |
| I | Ultrasonic Horn (Waveguide) | | |
| J | Solution Injection Jet | | |

FIG. 1

METHOD OF CREATING CRYSTALLINE SUBSTANCES

FIELD OF THE INVENTION

This invention relates to methods and apparatus for the creation and identification of cocrystals of active pharmaceutical ingredients with a guest molecule incorporated in their crystal structure using supercritical fluids technology.

BACKGROUND TO THE INVENTION

The process of development of an API (Active Pharmaceutical Ingredient) into the marketed dosage form can be challenging and time and resources consuming. This can often be attributed to limitations in terms of solubility, stability, bioavailability and processability into different dosage forms. Such limitations can be addressed by manipulating their solid form through a variety of formulation techniques including particle size and shape, solid phase, ionic (i.e. salt formation) and neutral (i.e. cocrystallisation) complexing to achieve the goal of improving their physicochemical characteristics and ultimately their pharmaceutical profile.

A pharmaceutical cocrystal is a form where a second molecule (usually called a guest molecule or coformer) is hydrogen bonded to the active substance to create an alternative form of the active substance with different physicochemical properties. It can be prepared by different methods including solvent crystallisation where both active substance and crystal former is dissolved in a single or mixture solvent system or each is dissolved separately and the solutions mixed to form the final solution that produce the cocrystal after solvent removal or phase separation. The cocrystal may then precipitate or crystallise as the solvent mixture is evaporated slowly. This process has also been automated to a high throughput screening system (see US2005/0267209).

Cocrystals have also been prepared by other methods including:

1. Crystallisation from the melt: A cocrystal may be obtained by melting the cocrystal components together and allowing recrystallisation to occur. In some cases, an anti-solvent may be added to facilitate crystallisation.
2. Thermal microscopy: A cocrystal may be obtained by melting the higher melting component on a glass slide and allowing it to recrystallise. The second component is then melted and is also allowed to recrystallise. The cocrystal may form as a separated phase/band in between the eutectic bands of the original components.
3. Mixing and/or grinding: A cocrystal may be obtained by mixing or grinding two or more components together in the solid state.
4. Solvent drop grinding: A cocrystal may be obtained by adding a small amount of organic solvents to a grinding of the components. (see Shan, N., Toda, F., Jones, W. Chem. Commun., 2002, 2372-2373).

Supercritical fluids (SCFs) have been used for extraction and fractionation of natural products such as decaffeination of coffee, extraction of essential oils from hop and spices. It's also been used in chromatography as mobile phases, medium for chemical reactions, dyeing of textiles and for particle formation. There are a large number of publications in the public domain where supercritical fluids in particular carbon dioxide has been used to control particle sizes and morphologies of sensitive materials such as pharmaceuticals (see WO 95/01221 and WO 99/59710, and U.S. Pat. No. 6,620,351) and been employed to perform polymorph screening of pharmaceuticals (see WO 2005/105293). The use of supercritical carbon dioxide in pharmaceutical processing is further described in Subramaniam et al., J. Pharm. Sci. 1997: 86, 8.

The scope for the work in active particle formation from SCFs was generally directed towards particle engineering and design of pure active substances or active substance and polymer system for controlled/sustained release of the API. In addition, the person skilled in the art would expect that particle formation of more than one pure, crystalline component/material of interest in a single solid structure to be problematic due to molecular incompatibility amongst other reasons that discourage nucleation and growth of both components in a single crystalline structure when the solvent system is removed rapidly by the SCF and more specifically when the SCF is used as anti-solvent and rapid deposition of crystals results. The molecular interactions between the solvent and pure components can greatly differ so as their nucleation and growth rates thus raising the likelihood of forming a physical mix of both pure compounds. Even if the product produced by supercritical fluid techniques (e.g. SEDS, SAS and SAS EM) looks uniform on physical examination or by certain solid state characterisation (e.g. SEM, particle size analysis), it is expected that PXRD analysis would show a profile of a mixture of both pure components, not an altogether different profile as the case tend to be with cocrystals. It is also expected that pure compounds could crystallise on top of each other due to the rapid solvent removal by the SCF, subsequent increase in solution super saturation and subsequent nucleation and growth.

STATEMENTS OF THE INVENTION

According to a first aspect of the present invention there is provided a process for preparing a cocrystal of an active substance and a cocrystal former, the process involving precipitating the active substance and the cocrystal former together from solution or suspension, in the presence of a supercritical or near-critical fluid.

The term "suspension" as used herein includes a suspension or dispersion of a solid in a liquid medium, a suspension or dispersion of a liquid in a liquid medium (emulsion), a micellar system or other system comprising one or more first phases suspended or dispersed in one or more second phases. The term "suspended" has a corresponding meaning.

According to a further aspect of the present invention there is provided a process for preparing a cocrystal of an active substance and a cocrystal former, the process involving precipitating the active substance and the cocrystal former together from solution, in the presence of a supercritical or near-critical fluid.

The cocrystal is preferably prepared in a particulate form.

The cocrystal former (which may also be known as a "guest molecule" or a "coformer") should be capable of hydrogen-bonding with the active substance so as to form a cocrystal as defined herein.

According to one embodiment, the active substance and the cocrystal former are dissolved or suspended in a supercritical or near-critical fluid, and are precipitated therefrom by a change in temperature and/or pressure, for instance by a rapid reduction in the pressure of the solution as in the known RESS process.

According to a second embodiment, the active substance and the cocrystal former are precipitated from solution or suspension by a supercritical or near-critical fluid anti-solvent, for instance using a GAS, SAS, SEDS or SAS-EM process of the type described below. Preferably the process is a SAS, SAS-EM or SEDS process, more preferably a SAS-EM or SEDS process as described more fully below.

The solution or suspension containing the active agents is then contacted with a supercritical fluid (e.g., supercritical carbon dioxide). Preferably, mixing is carried out by spraying the solution through a nozzle into a pressure chamber filled with the supercritical fluid. The supercritical fluid acts as an anti-solvent to precipitate materials dissolved in solvent and extract out the solvent. The active substance and the cocrystal former form a precipitate upon contact with the supercritical fluid.

In such a process wherein the active substance and the cocrystal former are dissolved or suspended in a solvent system which is subsequently contacted with a supercritical or near-critical fluid, it is preferred that the mixture of (a) the solution or suspension of the active substance and cocrystal former and (b) the supercritical or near-critical fluid is itself supercritical or near-critical.

Although the active substance and the cocrystal former should be precipitated together, ie, at substantially the same time and place, they may nevertheless be precipitated from separate solutions or suspensions.

The active substance may in particular be a pharmaceutically active substance. The cocrystal former is then suitably a pharmaceutically acceptable substance but may also be a pharmaceutically active substance if desired.

A second aspect of the invention provides a process for modifying a physicochemical property of an active substance, the process involving precipitating the active substance from solution or suspension together with a cocrystal former so as to form a cocrystal precipitate. Suitably the active substance and cocrystal former are co-precipitated in the presence of a supercritical or near-critical fluid, for example using a process according to the first aspect of the invention, preferably forming a supercritical or near-critical solution or suspension mixture.

The process of the second aspect of the invention may for example be used to modify one or more properties selected from solubility, dissolution profile, bioavailability, dose response profile, stability, saltability, hygroscopicity, morphology, polymorphic form and purity and restricting polymorphic form diversity. In particular it may be used to increase the crystallinity of the active substance.

The process may optionally involve measuring and/or comparing the relevant physicochemical property for both the active substance itself and the cocrystal containing it.

According to a third aspect, the invention provides a process for preparing a composition containing an active substance, in particular a pharmaceutical composition, the process involving forming a cocrystal of the active substance with a cocrystal former, suitably using a process according to the first aspect of the invention, and incorporating the cocrystal into a composition with one or more other substances.

A fourth aspect of the invention provides a cocrystal prepared using a method according to either the first or the second aspect. A fifth aspect provides a composition containing an active substance, the composition having been prepared using a method according to the third aspect.

A supercritical fluid is used herein to mean a fluid at or above its critical pressure ($P_c$) and critical temperature ($T_c$) simultaneously. In practice, the pressure of the fluid is likely to be in the range between 1.01 and 7.0 of its critical pressure, and its temperature in the range between 1.01 and 4.0 of its critical temperature (in Kelvin). However, some fluids (e.g., helium and neon) have particularly low critical pressures and temperatures, and may need to be used under operating conditions well in excess of those critical values, such as up to 200 times the relevant critical value.

The term "near-critical fluid" encompasses both high pressure liquids, which are fluids at or above their critical pressure but below (although preferably close to) their critical temperature, and dense vapors, which are fluids at or above their critical temperature but below (although preferably close to) their critical pressure.

By way of example, a high pressure liquid might have a pressure between about 1.01 and 7 times its $P_c$, and a temperature between about 0.5 and 0.99 times its $T_c$. A dense vapour might, correspondingly, have a pressure between about 0.5 and 0.99 times its $P_c$, and a temperature between about 1.01 and 4 times its $T_c$.

Any suitable supercritical fluid may be used in the process of the present invention. The supercritical fluid should be compatible with the active agents that are dissolved in or contacted with the supercritical fluid in the crystallisation processes detailed herein.

Typical supercritical fluids and their critical properties (i.e., critical temperature, critical pressure, and critical density) are listed in Table 1.

TABLE 1

Critical Parameters of Selected Fluids.

| Fluid | $T_c$ (° C.) | $P_c$ (MPa) | $\rho_c$ (g/cm³) |
|---|---|---|---|
| ethylene | 9.3 | 5.04 | 0.22 |
| xenon | 16.6 | 5.84 | 0.12 |
| carbon dioxide | 31.1 | 7.38 | 0.47 |
| ethane | 32.2 | 4.88 | 0.20 |
| nitrous oxide | 36.5 | 7.17 | 0.45 |
| propane | 96.7 | 4.25 | 0.22 |
| ammonia | 132.5 | 11.28 | 0.24 |
| n-butane | 152.1 | 3.80 | 0.23 |
| n-pentane | 196.5 | 3.37 | 0.24 |
| isopropanol | 235.2 | 4.76 | 0.27 |
| methanol | 239.5 | 8.10 | 0.27 |
| toluene | 318.6 | 4.11 | 0.29 |
| water | 374.2 | 22.05 | 0.32 |

Carbon dioxide is preferably utilised as the supercritical fluid for producing pharmaceutical formulations containing at least one active substance and at least one cocrystal former according to the present invention.

Supercritical Fluid Crystallisation.

The use of supercritical fluids—and the properties thereof has been extensively documented; see for instance, J. W. Tom and P. G. Debenedetti, review on "Particle Formation with Supercritical Fluids—A Review", J. Aerosol. Sci., 22 (5), 555-584 (1991). Supercritical fluids have been of considerable interest, not least because of their unique physicochemical properties including; high diffusivity, low viscosity and low surface tension compared with liquids. As used herein the abbreviation "SCF" includes both supercritical fluids and near-critical fluids.

Large compressibility of supercritical fluids compared with the ideal gas implies large changes in fluid density for slight changes in pressure, which in turn results in highly controllable solvation power. Supercritical fluid densities typically range from 0.1-0.9 g/ml under normal working conditions. Thus, selective extraction with one supercritical fluid is possible.

Many supercritical fluids are normally gases under ambient conditions, which eliminate the evaporation/phase separation step needed in conventional liquid crystallisation.

Most of the commonly used supercritical fluids create non-oxidizing or non-degrading atmospheres for sensitive and thermo labile compounds, due to their inertness and the moderate temperatures used in routine working conditions. Carbon dioxide is the most extensively used SCF due to its cheapness, non-toxicity, non-flammability and low critical temperature.

Examples of preferred supercritical processing techniques for crystallisation or cocrystallisation or particle formation of pharmaceuticals include Rapid Expansion from Supercritical Solutions (RESS), Gas Antisolvent (GAS), Supercritical Anti-Solvent (SAS), and Supercritical Antisolvent Precipitation with Enhanced Mass Transfer (SAS-EM). In accordance with the present invention, cocrystals can be produced using a variety of different SCF particle formation techniques including but not limited to supercritical fluid extraction of emulsions (SFEE), Spray Freeze Drying (SFD) with compressed $CO_2$ (see Chattopadhyay, P., Shekunov, B. Y., Drug Delivery Technology, Vol. 6, No. 8, pp 64-68) and DELOS (Depressurisation of an Expanded Liquid Organic Solution) (see J. supercritical fluids, 2003, vol. 26, No. 1, pp 33-45). There are also other SCF processes and variations aimed at producing particles or crystals/cocrystals; cocrystals can also be produced by many if not all of such processes.

RESS

Rapid Expansion of Supercritical Solution (RESS) (see, for instance, J. W. Tom and P. G. Debenedetti, supra) involves the dissolution of the solute of interest in the supercritical fluid, followed by rapid expansion of the supercritical solution to atmospheric pressure, resulting in the precipitation of particles.

In the RESS process, the active substance and the cocrystal former are dissolved in a supercritical fluid, preferably carbon dioxide, to form a homogenous solution. Other excipients or second cocrystal formers may optionally be added to the supercritical fluid. The active substance and the cocrystal former may be added to the supercritical fluid simultaneously or in other suitable order. The resulting solution is then passed through an orifice or nozzle into a chamber. Preferably, the pressure in the chamber is atmospheric. By spraying the homogenous solution through an orifice or nozzle, the solution is depressurised rapidly resulting in the vaporisation of the carbon dioxide or other supercritical fluid. The active agents and optional excipients are crystallised as a uniform mixture in dry powder form.

RESS can be used if the active substance and the cocrystal former to be precipitated are soluble in the supercritical fluid, such as supercritical carbon dioxide. If the active agents are not readily soluble in the supercritical fluid, the active agents may be first dissolved or suspended in a cosolvent system and then added to the supercritical fluid. The cosolvent may be a single solvent or two or more solvents combined together. Alternatively, the cosolvent may be added to the supercritical fluid initially followed by the addition of the active agents to the mixture of the supercritical fluid and cosolvent. When a cosolvent is required, the cosolvent used generally has a higher dielectric constant than the supercritical fluid (e.g., supercritical carbon dioxide), but is miscible in the supercritical fluid.

Examples of suitable solvents and cosolvents include 1-pentanol, 1-propanol, 2-methyl-1 propanol, 2-propanol, acetone, butane, butanol, butrylactone, carbon dioxide, carbon tetrachloride, chloroform, cyclohexane, cyclohexanone, dichloromethane, dimethylsulfoxide, ethane, ethanol, ethyl acetate, ethyl ether, ethyl formate, fluoroform, heptane, hexane, isbutyl acetate, isobutene, isopropyl acetate, methanol, methylene chloride, methylethylketone, methylisobutylketone, N,N dimethylformamide, nitrous oxide, pentane, propane, sulfur hexafluoride, tetrahydrofuran, toluene, water, and combinations thereof. Other suitable solvents include those compounds known in the art in which the active pharmaceutical ingredients to be blended can be dissolved or suspended.

GAS

Gas Anti Solvent (GAS) Recrystallisation (P. M. Gallagher et al, Supercritical Fluid Science and Technology, ACS Symp. Ser., 406, p 334 (1989)) is particularly useful in situations when the solid of interest does not dissolve in, or has a very low solubility in, a supercritical fluid or a modified supercritical fluid. In the GAS process, supercritical carbon dioxide is added to a solution or suspension of the desired active pharmaceutical ingredients dissolved or suspended in an organic cosolvent. In practice, the solution of the active agents is pumped into a pressure vessel and the SCF (e.g. $CO_2$) is slowly added to the solution or suspension. Supercritical carbon dioxide and organic solvent are miscible whereas the solid active agents have limited solubility in carbon dioxide. Thus, the carbon dioxide acts as an antisolvent to precipitate cocrystals of the active agents. The depleted solution or suspension is then forced out of the vessel and the cocrystallised particulate product flushed with liquid/sc $CO_2$ to dry the product. The system depressurized and product recovered.

The supercritical fluid may optionally be mixed with one or more cosolvents prior to the addition of the solution or suspension containing the active agents.

SAS

Another suitable process for crystallisation according to the present invention is the SAS process. The SAS technique is well-suited for precipitation of active agents that are only slightly soluble in the supercritical fluid of interest, such as supercritical carbon dioxide.

In the SAS process, the active substance and the cocrystal former are dissolved or suspended in a solvent system. The solvent may be any suitable liquid containing one or more solvents in which the active agents are dissolved or suspended. The solvent is also miscible in the supercritical fluid. Examples of solvents suitable for use in the SAS method include those solvents discussed herein that may be used in the RESS process as cosolvents as well as other solvents in which the active agents can be dissolved or suspended.

The solution or suspension containing the active agents is then contacted with a supercritical fluid (e.g., supercritical carbon dioxide). Preferably, mixing is carried out by spraying the solution or suspension through a nozzle into a pressure chamber filled with the supercritical fluid. The supercritical fluid acts as an anti-solvent to precipitate materials dissolved in solvent and extract out the solvent. The active substance and the cocrystal former form a precipitate upon contact with the supercritical fluid. This can be attributed to dramatic decrease in solvent dissolution power due to free miscibility with the SCF resulting in significant increase in solution supersaturation triggering nucleation, growth and precipitation of cocrystals. The crystalline product containing the active pharmaceutical ingredients and any optional excipients is then recovered after flushing the chamber with fresh supercritical fluid and depressurizing it.

The supercritical fluid may optionally be mixed with one or more cosolvents prior to the addition of the solution or suspension containing the active agents.

SEDS

SEDS (Solution Enhanced Dispersion by Supercritical Fluids) also named as NEKTAR Supercritical Fluid Technology is a process in which a solution or suspension of the active agents or materials of interest, in an appropriate solvent system, is co-introduced into a pressure vessel with a supercritical fluid (e.g. $CO_2$), in such a way that dispersion and extraction of the solvent occur substantially simultaneously by the action of the supercritical fluid, and substantially immediately on introduction of the fluids into the vessel. The pressure and temperature inside the particle formation vessel are carefully controlled during this process. The cocrystallised product precipitated and retained by a filter in the vessel and the emerging supercritical solution ($CO_2$ and solvent system) is vented after the back pressure regulator. At the end of the process the vessel is flushed with copious amounts of fresh $CO_2$, system depressurised and products collected. In the SEDS process the SCF and the solution or suspension of material(s) of interest may be co-introduced into the pressure vessel via a coaxial nozzle, for example of the type described in WO-95/01221 or WO-96/00610. The fluids may be co-introduced using a modified fluid inlet of the type described in WO-03/008082 or WO-2004/062785.

SEDS allows a high degree of control over conditions such as pressure, temperature and fluid flow rates, and over the physical dispersion of the solution/suspension, at the exact point where particle formation occurs (i.e. at the point where the vehicle is extracted into the supercritical fluid). It therefore allows excellent control over the size, shape and other physical and/or chemical properties of the particles formed.

SAS-EM

SAS-EM provides a novel way to produce fine particles with narrow size distribution. The SAS-EM uses a supercritical fluid as the antisolvent, but the dispersion of solution is made by a vibrating surface that atomises the jet into microdroplets or dispersion. The solution or suspension of active agents is pumped under pressure as a jet onto the vibrating surface causing a thin, evenly spread liquid film. A set of wavelets then form on the free liquid layer due to the vibrating surface. The oscillatory vibrations of the liquid surface causes these wavelets to increase in amplitude until the wavelet tips break off and the droplets are emitted from the surface into the supercritical fluid media. Rapid transfer of $CO_2$ into these droplets and the solvent out of these droplets causes them to expand rapidly, leading to a decrease in the droplet's ability to keep the solute molecules dissolved causing the molecules to precipitate as fine cocrystals. The vibration field generated by the vibrating surface inside the supercritical phase helps enhancing mass transfer between the solvent and the supercritical fluid due to increased turbulence and mixing.

SAS-EM uses high frequency vibrations for atomisation of solution. Any tube made of a standard material (for example: Stainless Steel, Fused Silica) can be used to inject the solution or suspension of the active materials of interest onto the vibrating surface (for instance an acoustic horn). The diameter of the tube can be varied and subsequently the amount of solution or suspension dispersed to effect control over particle size.

It should be noted that the SAS-EM process is different in principle from the conventional use of ultrasound for the promotion of crystallisation in bulk solutions. It is well known to use ultrasound as an aid to promote nucleation and hence crystallisation within the bulk of a saturated or near saturated solution of a crystallisable substance in a suitable solvent. In contrast, the SAS-EM process uses the high frequency vibration to create surface instability and subsequently solution film instability which results in the dispersion of the solution into a fine droplet spray thus increasing the surface area of the solution and improving the two way mass transfer between the solution and the SCF as described above.

The SAS-EM process is described in for instance U.S. Pat. No. 6,620,351. Its operation is further described below with reference to FIG. 1, in which the particle formation vessel 'L' is heated to the required process temperature by a thermostatically controlled heating jacket 'K'. The vessel is then pressurised to the required process pressure by a Carbon Dioxide Pump 'D'.

The process stream for the Carbon Dioxide begins with a liquefied bulk storage cylinder 'A'. Liquid Carbon Dioxide is fed from cylinder 'A' through a sub-cooling heat exchanger, to ensure that a single phase liquid is present at the inlet to pump 'D'. Pump 'D' is electronically controlled by a mass flow meter 'M' such that a constant mass flow of $CO_2$ is fed into the system, irrespective of system pressure.

The liquid Carbon Dioxide from pump 'D' is pressurised by the pump and passed through a thermostatically controlled heat exchanger 'F', which elevates the Carbon Dioxide to the required process temperature. It is then introduced into the pressure vessel through a side port on the vessel.

The drug solution (or suspension) is pumped from the drug solution container 'B' through a high pressure metering pump 'C'. A constant flow of drug solution is maintained at the desired rate by mass flow meter 'M'. The pressurised drug solution from pump 'C' is passed through a heat exchanger 'E', which elevates the drug solution to the required process temperature.

On entering the particle formation vessel, the drug solution is fed to a narrow bore solution jet 'J' which is arranged in close proximity and at an angle to the tip of an ultrasonically excited horn or waveguide 'I'. The ultrasonic horn 'I' is excited by a Piezo-electric drive cell 'H', which is connected electronically to a variable amplitude control system.

The narrow bore solution jet 'J' causes a jet of drug solution to be propagated onto the surface of, or into the near region of the ultrasonically excited horn 'I' where, depending on process conditions, it is either broken into fine droplets, or is rapidly dispersed and mixed with the $scCO_2$. The antisolvent properties of the $scCO_2$ initiate rapid supersaturation of the solute within the solvent, causing nucleation and the formation of fine particulates of the cocrystals of interest. The size and morphology of such cocrystals may be varied by making one or more adjustments to the amplitude of the ultrasonic excitation, and/or to the process conditions.

The cocrystals are retained within the particle formation vessel by a porous filter membrane 'N', or by means of a filter bag, or may be continuously swept from the particle formation vessel by the effluent gas to be separated in a down stream process, such as cyclonic separation.

The system is maintained at the required process pressure by means of an automated back pressure regulator valve 'Q'. The valve contains an automated system whereby the upstream vessel pressure generates a feedback control signal to an actuator on the valve spindle, regulating the outlet pressure from the vessel.

The back pressure regulator 'Q' may drop the system pressure to atmospheric pressure in one stage, or may regulate both the upstream and downstream pressures to facilitate the separation of the solvent from the Carbon Dioxide within a downstream vent abatement system.

The pressure drop across the back pressure regulator may generate a significant temperature drop in the $CO_2$ and to prevent the exit line freezing, a vent line heat exchanger 'R' is fitted close to the downstream side of the back pressure regulator.

A solvent separation and collection system 'S' is fitted to the effluent gas stream to the system, in order to reduce the level of volatile organic compounds within the effluent gas. This may be achieved by such means as (but not limited to) absorption, cryogenic separation, distillation, or cyclonic separation.

The particle morphology can also be controlled by SAS EM by changing the input power intensity to the vibration source. This changes the amplitude of vibrations of the horn surface. Change in intensity also produces narrower particle size distribution.

It must be noted that SAS EM will be used to conduct experimental work of this invention though other suitable processes known to those persons of ordinary skill in the art that involve a supercritical fluid, preferably supercritical carbon dioxide, may be used to crystallise combinations of active substances and cocrystal formers.

BRIEF SUMMARY OF THE INVENTION

The present invention provides a method and apparatus for the formation of cocrystals by dissolving the active substance and a cocrystal former in a suitable solvent system normally though not necessarily an organic solvent and removing the solvent through the use of a supercritical fluid under favorable conditions that encourage formation of a solid phase.

BRIEF DESCRIPTION OF THE DRAWINGS

FIG. 1. Schematic diagram of the SAS EM apparatus.

DETAILED DESCRIPTION OF THE INVENTION

Definitions

Figure 2:
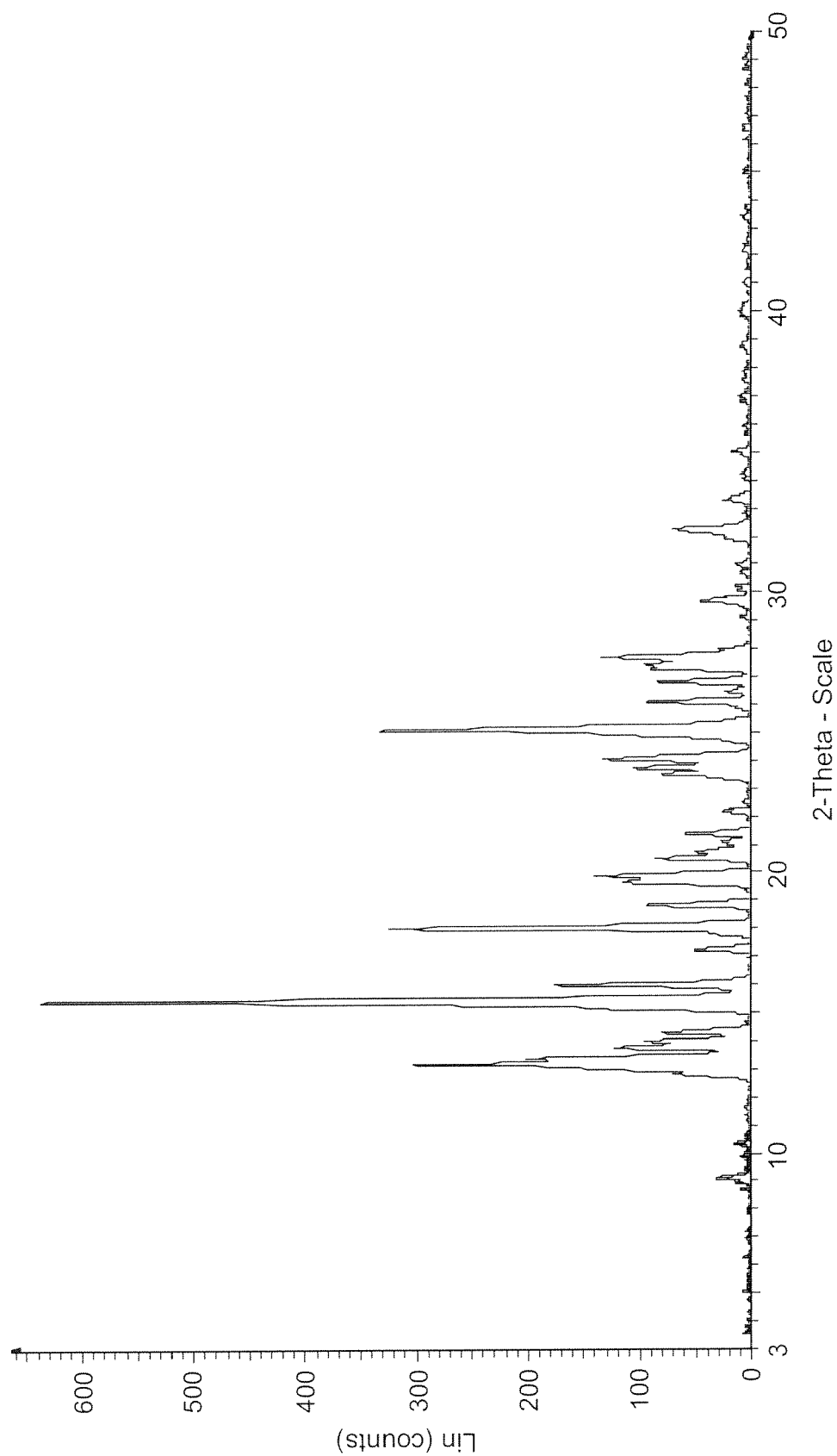
FIG. 2. PXRD pattern of CBZ (carbamazepine)-aspirin prepared at 90 bar and 35° C.

As used herein, the following terms have the following respective meanings.

Cocrystal (or co-crystal) is used herein to mean a crystalline material comprised of two or more unique solids at room temperature (22 degrees C.), each containing distinctive physical characteristics, such as structure, solubility, melting point, and heats of fusion, with the exception that, if specifically stated, the active substance may be a fluid at room temperature.

The cocrystals of the present invention comprise a cocrystal former (a "guest molecule" or "coformer") hydrogen bonded (H-bonded) to an active substance such as an API, agrochemical, nutraceutical, excipient, permeation enhancer, or other functional molecule. The cocrystal former may be H-bonded directly to the active substance or may be H-bonded to an additional linking molecule which is bound to the active substance. The additional molecule may be H-bonded to the active substance or bound ionically or covalently to it. The additional molecule could also be a different active substance. Solvates of an active substance that do not further comprise a cocrystal former are not cocrystals according to the present invention. The cocrystals may however, include one or more solvate molecules in the crystalline lattice. That is, a solvate of a cocrystal, or a cocrystal further comprising a solvent or compound that is a liquid at room temperature, is a cocrystal according to the present invention, but crystalline material comprised of only one solid and one or more liquids (at room temperature) are not cocrystals for purposes of the present invention, with the previously noted exception of specifically stated liquid active substances.

The cocrystals may also be a cocrystal between a cocrystal former and a salt of an active substance, but the active substance and the cocrystal former of the present invention are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the cocrystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

An "active substance" can be a pharmaceutical, agrochemical, nutraceutical, excipient, permeation enhancer, or other functional molecule.

"Antisolvent" means a fluid that acts as a non solvent to the material of interest (cocrystal) and precipitates or crystallises it. Anti-solvent refers to a fluid existing at a temperature around the pure fluid critical temperature and pressure. Therefore, the term anti-solvent includes supercritical fluids, compressed liquefied gases and dense vapors. Because the anti-solvent is chosen from substances that have very small equilibrium solubility for the material of interest, the anti-solvent is a non-solvent in this process.

"Close to the vibrating surface" means close enough to the vibrating surface so as to get exposed to at least one wavelength of vibration. Typically one wavelength of vibration with 20 Khz frequency in the vessel is about 2 cm.

"Collecting the particles in a continuous manner" means collection of the produced particles in a manner that does not require stopping the production of particles.

"Compressed antisolvent" means an antisolvent at a compressed state, i.e. at a higher pressure than the atmospheric pressure.

"Core particles" means particles that are to be coated or surrounded by the desired substance.

"Desired substance" means the material comprised of one or more active substance.

"Dispersant" means a fluid that helps in dispersing or scattering a material in a medium.

"Dispersion" when referring to a mixture containing a fluid means the result of a dispersion process; a homogeneous or heterogeneous mixture of the desired substance in one or more suitable solvents with or without dispersants. "Dispersion" when referring to an act carried out on a fluid (ie, when used as a nominalised verb) means the breaking up of the fluid into individual fluid elements, for example droplets.

"Droplets" means a relatively small drop or entity of solution or suspension that can exist independently in the supercritical fluid medium.

"Enclosed space" means a space enclosed by a metal or any other material.

"Intensity of the vibration" means the degree of vibration or the extent to which the surface vibrates. It is directly proportional to the input power to the vibrating source. Higher the intensity of vibration greater is the amplitude of vibrating the surface.

"Material of interest" means one or more active substances desired for processing by the invention.

"Miscible" means two substances being soluble in each other at all proportions.

"Morphology of the particle" means external structural appearance or the form of the particle.

"Near or supercritical conditions" means the temperature and pressure of the fluid being closer to or higher than the critical temperature and critical pressure of the fluid respectively. Preferably, the temperature being from $0.7 T_c (K)$ to $1.5 T_c (K)$ and pressure being from $0.2 P_c$ to $10 P_c$.

"Particles" means a particle is a relatively small discrete portion of the material of interest.

"Piezoelectric" means a material capable of generating vibrations when subjected to applied voltage.

"Polymorph" means different crystalline or non-crystalline structures of a solid material. It includes the amorphous form and various solvate, hydrate forms commonly referred to as pseudo polymorphs. Different polymorphs have different free energy associated with them.

"Solvent system" means a fluid or a combination of fluids, which can dissolve the desired substance in order to form a homogenous solution.

"Suspension" means a suspension or dispersion of a solid in a liquid medium, a suspension or dispersion of a liquid in a liquid medium (emulsion), a micellar system or other system comprising one or more first phases suspended or dispersed in one or more second phases. The term "suspended" has a corresponding meaning.

"Supercritical solution" means a solution of a substance and/or another fluid, in a supercritical fluid, the solution itself being in a supercritical state. The term "near-critical solution" means a solution, itself in a near-critical state, of a substance and/or fluid in a near-critical fluid.

"Substantially insoluble in the antisolvent" means the desired substance has no or very little solubility in the antisolvent.

"Vibrating surface" generally means the exterior or the boundary of an acoustic horn tip excluding any nozzle surface onto which the dispersion is sprayed.

"Vibrating the surface" means moving the surface at a rapid rate by means of an external source.

Cocrystal Description

The cocrystals of the present invention are formed where the active substance and cocrystal forming compound are bonded together through hydrogen bonds. Other non-covalent interactions, including pi-stacking and van der Waals interactions, may also be present.

Those skilled in the art will be aware of suitable active substances and partner cocrystal formers that have the potential for hydrogen bonding and subsequent cocrystal formation. The present invention provides a convenient and efficient process for cocrystal formation, even for active substances and cocrystal formers that are difficult to cocrystallise using conventional methods. Certain functional groups such as carboxylic acid, amides and alcohols (and their acid addition salts or base addition salts as the case may be) are particularly amenable to formation of non-covalent hydrogen bonding with complementary functional groups. In particular there may be mentioned cocrystal formation between a substance containing an acidic moiety or a salt thereof such as a carboxylic acid group or a salt thereof and a cocrystal former also containing an acidic moiety or a salt thereof such as a carboxylic acid group or a salt thereof. A further combination of active substance and cocrystal former which is especially suitable for use in the present invention is provided by the hydrogen bonding interaction between a acidic moiety or a salt thereof and the nitrogen atom of an aromatic nitrogen heterocycle such as pyridine or a pyridine derivative or a base addition salt thereof. It will be appreciated that the acidic moiety may be present in the active substance and the aromatic nitrogen moiety in the cocrystal former or the acidic moiety may be present in the cocrystal former and the aromatic nitrogen in the active substance.

Thus according to the present invention, the cocrystals can include an acid addition salt or base addition salt of an active substance. Acid addition salts include, but are not limited to, salts of inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, salts of inorganic bases such as sodium, potassium, lithium, ammonium, calcium and magnesium salts, and organic bases such as primary, secondary and tertiary amines (e.g. isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, and N-ethylpiperidine).

It has surprisingly been found that when an active substance and a selected cocrystal forming compound are allowed to form cocrystals, the resulting cocrystals may give rise to improved properties of the active substance, as compared to the active substance in a free form (including free acids, free bases, and zwitter ions, hydrates, solvates, etc.), or an acid or base salt thereof particularly with respect to: solubility, dissolution, bioavailability, stability, $C_{max}$, $T_{max}$, processability, longer lasting therapeutic plasma concentration, hygroscopicity, crystallisation of amorphous compounds, decrease in form diversity (including polymorphism and crystal habit), change in morphology or crystal habit, etc. For example, a cocrystal form of an active substance is particularly advantageous where the original active substance is insoluble or sparingly soluble in water. Additionally, the cocrystal properties conferred upon the active substance are also useful because the bioavailability of the active substance can be improved and the plasma concentration and/or serum concentration of the active substance can be improved. This is particularly advantageous for orally-administrable formulations. Moreover, the dose response of the active substance can be improved, for example by increasing the maximum attainable response and/or increasing the potency of the active substance by increasing the biological activity per dosing equivalent.

Accordingly, the present invention provides a pharmaceutical composition comprising a cocrystal of an active substance and a cocrystal forming compound, such that the active substance and cocrystal forming compound dissolved or suspended in a solvent system are capable of cocrystallizing from a supercritical solution or suspension of the solvent and SCF.

Typical functional groups which may be present in the active substance include at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine. Typical functional groups which may be present in the cocrystal forming compound include at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine, or other functional groups known to the skilled person in the art, such that the active substance and cocrystal forming compound are capable of cocrystallizing from a supercritical solution phase under process conditions.

In another aspect, the difference in $pK_a$ value of the cocrystal former and the active substance is preferably less than 2. In general, if the $pK_a$ value of the cocrystal former and the active substance exceeds 2, then the formation of a salt rather than a cocrystal is more likely.

In yet another aspect of the invention, the cocrystal comprises more than one cocrystal former. For example, two, three, four, five, or more cocrystal formers can be incorporated in a cocrystal with an active substance. Cocrystals which comprise two or more cocrystal formers and an active substance are bound together via hydrogen bonds. In one aspect, incorporated cocrystal formers are hydrogen bonded to the active substance molecules only. In another aspect, cocrystal formers are hydrogen bonded to either the active substance molecules or other incorporated cocrystal formers.

Specific examples of suitable active substances and cocrystal formers are listed for example in US-A-20070026078 published Jan. 2, 2007. Other examples of suitable active substances and cocrystal formers are published in the general literature available to one skilled in the art.

The ratio of active substance to cocrystal former may be stoichiometric or non-stoichiometric according to the present invention. For example, 1:1, 1:1.5 and 1:2 ratios of active:cocrystal former are acceptable.

It is preferred that the molar ratio of the active substance to the cocrystal former is substantially stoichiometric. The stoichiometric ratio of active substance to cocrystal is commonly 1:1 but those skilled in the art will appreciate that other stoichiometries are possible depending on the crystal structure. Thus as noted above, examples of possible stoichiometries include ratios of active substance to cocrystal former of 1:1, 1:1.5, 1:2 or a few instances 1:3. Conversely the ratio of the cocrystal former to active substance may be 1:1.5, 1:2 or 1:3. For example a cocrystal of aspirin (acetylsalicylic acid) and 4,4'-bipyridine may give rise to carboxylic acid-pyridine heterodimer in the cocrystal structure resulting in 2:1 stoichiometry. A stoichiometric ratio of active substance to cocrystal former of 1:3 or higher is rare and at such ratios the formation of clathrates is more likely than cocrystal formation. By the term "substantially stoichiometric" is meant a molar ratio within 20% of the stoichiometric value, preferably within 10% of the stoichiometric value more preferably within 5% of the stoichiometric value and still more preferably within 2% of the stoichiometric value. Thus for example a molar ratio within 10% of a stoichiometric value of 1:1 means a molar ratio of from 0.9:1 to 1.1:1. Similarly a molar ratio within 10% of a stoichiometric value of 1:2 means a molar ratio of from 0.9:2 to 1.1:2.

In each process according to the invention, there is a need to contact the molecules of the active substance with that of cocrystal forming compound preferably in a solvent. This may also involve either solubilizing the active substance and adding the cocrystal forming compound, or solubilizing the cocrystal forming compound and adding the active substance. Or solubilizing both the active substance ad cocrystal former in the same or different solvent system and adding the solvents together to form a solution or suspension that can subsequently fed to the apparatus of the current invention. Crystallisation conditions are applied to the active substance and cocrystal forming compound. This may entail altering a property of the solution or suspension, such as pH, temperature, pressure and may require also altering the concentration of the solute, usually by removal of the solvent, typically by the SCF. Solvent removal results in the concentration of both active substance and cocrystal former increasing over time so as to facilitate crystallisation.

The cocrystals obtained as a result of the process of the present invention may be readily incorporated into a pharmaceutical composition by conventional means. Pharmaceutical compositions in general are discussed in further detail below and may further comprise a pharmaceutically-acceptable diluent, excipient or carrier.

Alternatively, the cocrystals formed by the process of the present invention may be used as seeds for the nucleation and precipitation from solution of cocrystals using conventional techniques or any of the techniques described herein. Solutions of the active substance and the potential cocrystal former that may be difficult to crystallise at all or that may crystallise as a mixture of crystals may nevertheless crystallise in the desired cocrystal form if seeded using known techniques with cocrystals prepared by the process of the present invention. It may be commercially preferred to prepare seed cocrystals using the process of the present invention and then use such seed cocrystals for the commercial scale precipitation of the desired cocrystals from solution.

Thus according to a further aspect of the present invention there is provided a process for the preparation of a cocrystal of an active substance and a cocrystal former which comprises precipitating a cocrystal from a solution of an active substance and a cocrystal former in the presence of a seed crystal prepared by a process of the present invention.

The term "polar aprotic" refers to solvents which do not contain hydroxy groups but have a relatively high dipole moment. Polar aprotic solvents useful in the solvent mixtures of the present invention include acetonitrile, N,N-dimethylformamide (DMF), dimethyl sulfoxide (DMSO), 1,1-dimethoxyethane (DME), hexamethylphosphoric triamide (HMPA), and the like.

In a further aspect, the present invention provides a process for the production of a composition containing an active substance (e.g. a pharmaceutical composition), which process comprises:

(a) providing an active substance which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile diazo, organohalide, nitro, S-heterocyclic ring, thiophene, N-heterocyclic ring, pyrrole, O-heterocyclic ring, furan, epoxide, peroxide, hydroxamic acid, imidazole, and pyridine;

(b) providing a cocrystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine;

(c) contacting a solution or suspension (in conventional or supercritical fluid solvent system) of the active substance with the cocrystal forming compound with a SCF (e.g. $CO_2$) antisolvent under supercritical conditions to remove the solvent (d) separating the solid phase from the supercritical solution (e) collecting the cocrystals formed (product) in a continuous or semi batch manner; and (f) incorporating the cocrystals into a composition.

In a still further aspect the present invention provides a process for the production of a composition such as a pharmaceutical composition, by heating the solution or suspension of the active substance with a cocrystal forming compound in a heat exchanger prior to contacting with SCF whether at the same or higher temperature to that of the SCF crystallisation process and carrying out steps c to e, and optionally f, as above.

Moreover, the present invention provides a process of producing cocrystal compounds, by pressurizing the solution or suspension of the active substance and cocrystal former for a period of time before contacting with the SCF followed by steps c to e, and optionally f, as above.

The present invention also provides methods for testing the prepared cocrystals (product) by using thermal analytical techniques such as differential scanning calorimetry (DSC) and thermogravimetric analysis (TGA) where the product has an endotherm different to that of the solid physical mix of the active substance and cocrystal former.

It also provides the means to test the product spectroscopically by using powder x-ray diffraction method (PXRD) or Raman or IR, or near IR, etc. However, PXRD will be the main testing technique where the diffractogram of the cocrystal product differs from that of the solid physical mix of the parent materials (active substance and cocrystal former) or that of pure active substance and cocrystal former.

In another aspect of the invention, the opportunity is provided to obtain different polymorphs of the cocrystal product by manipulating the process working conditions of pressure, temperature, the rate of SCF to solution addition and the like. This can be tested using thermal or spectroscopic analytical methods as stated previously.

The different polymorph of the product is created in such a form that it has different physicochemical properties versus the original active substance or original cocrystal product. Such differences include but are not limited to:

1 Solubility Modulation

The present invention provides a process for modulating the aqueous solubility of an active substance such as an API, which process comprises:

(1) Contacting in solution the active substance with a cocrystal forming compound under supercritical or subcritical crystallisation conditions, so as to form cocrystals of the active substance and the cocrystal forming compound, (2) Isolating the cocrystal product (the active substance and the cocrystal forming compound), and (3) Measuring the aqueous solubility of the product and comparing it with that of the original active substance at 37° C. using analytical techniques such as HPLC or GC or spectroscopic methods such as UV or mass spectroscopy.

The active substance may have low aqueous solubility. Typically, low aqueous solubility in the present application refers to a compound having a solubility in water which is less than or equal to 10 mg/mL, when measured at 37° C., or less than or equal to 1 mg/mL. This invention can provide a substantial increase in aqueous solubility of the product by a factor between 2 and 10,000 times compared to that of the active substance under identical analysis conditions. Further, aqueous solubility can be measured in simulated gastric fluid (SGF) or simulated intestinal fluid (SIF) rather than pure water. SGF (non-diluted) of the present invention is made by combining 1 g/L Triton X-100 and 2 g/L NaCl in water and adjusting the pH with 20 mM HCl to obtain a solution with a final pH=1.7 (SIF is 0.68% monobasic potassium phosphate, 1% pancreatin, and sodium hydroxide where the pH of the final solution is 7.5). The pH of the solvent used may also be specified as any value between 1 and 12.

Cocrystal compositions produced by the method of the invention can offer at least 5 fold increase in aqueous solubility, at 37° C. and a pH of 7.0. It can also provide a 5 fold enhanced solubility in SGF and SIF at 37° C. compared with the original active substance.

2 Dissolution Modulation

In another aspect of the present invention, the dissolution profile of the active substance is modulated whereby the aqueous dissolution rate or the dissolution rate in simulated gastric fluid or in simulated intestinal fluid, or in a solvent or plurality of solvents is increased. Dissolution rate is the rate at which active substance solids dissolve in a dissolution medium. For active substances whose absorption rates are faster than the dissolution rates (e.g., steroids), the rate-limiting step in the absorption process is often the dissolution rate. Because of a limited residence time at the absorption site, active substances that are not dissolved before they are removed from intestinal absorption site are considered useless. Therefore, the rate of dissolution has a major impact on the performance of active substances that are poorly soluble. Because of this factor, the dissolution rate of active substances in solid dosage forms is an important, routine, quality control parameter used in the active substance manufacturing process.

$$\text{Dissolution rate} = KS(C_s - C)$$

where K is dissolution rate constant, S is the surface area, $C_s$ is the apparent solubility, and C is the concentration of active substance in the dissolution medium.

For rapid active substance absorption, $C_s-C$ is approximately equal to $C_s$.

The rate of dissolution of active substances may be measured by conventional means known in the art.

The increase in the dissolution rate of a cocrystal, as compared to the reference form (i.e. active substance), may be specified, such as by any value between 5 and 10,000 fold greater than the reference form in the same solution. Conditions under which the dissolution rate is measured is the same as discussed above. The increase in dissolution may be further specified by the time the composition remains supersaturated before reaching equilibrium solubility.

Examples of above embodiments include: cocrystal compositions with a dissolution rate in aqueous solution, at 37° C. and a pH of 7.0, that is increased at least 5 fold over the reference form, cocrystal compositions with a dissolution rate in SGF that is increased at least 5 fold over the reference form, cocrystal compositions with a dissolution rate in SIF that is increased at least 5 fold over the reference form.

3 Bioavailability Modulation

The methods of the present invention are used to make an active substance formulation, in particular of a pharmaceutically active substance, with greater solubility, dissolution, and bioavailability. Bioavailability can be improved via an increase in AUC (area under the curve), reduced time to $T_{max}$, (the time to reach peak blood serum levels), or increased $C_{max}$. The present invention can result in higher plasma concentrations of active substance when compared to the reference form (pure active substance).

AUC is the area under the curve of plot of plasma concentration of active substance (not logarithm of the concentration) against time after active substance administration. The area is conveniently determined by the "trapezoidal rule": The data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of APIs, and in estimating total clearance of APIs ($Cl_T$). Following single intravenous doses, $AUC=D/Cl_T$, for single compartment systems obeying first-order elimination kinetics, where D is the dose; alternatively, AUC=C.sub.0/k.sub.el, where k.sub.el is the active substance elimination rate constant. With routes other than the intravenous, for such systems, $AUC=F.multidot.D/Cl_T$, where F is the absolute bioavailability of the API.

Thus, in an aspect of the present invention, it provides a process for modulating the bioavailability of an active substance when administered in its normal and effective dose range as a cocrystal, whereby the AUC is increased, the time to $T_{max}$ is reduced, or $C_{max}$ is increased, as compared to a reference form (pure active substance) where cocrystal compositions with a time to $T_{max}$ is reduced by at least 20% to at least 80% (or any value in between) as compared to the reference form. In addition, cocrystal compositions with a $C_{max}$ that is increased by at least 20% to at least 90% (or any value in between) over the reference form, cocrystal compositions with a C.sub.max that is increased by at least 2 fold to 100 fold (or any value in between), cocrystal compositions with an AUC that is increased by at least 10% to at least 80% (or any value in between) over the reference form, or cocrystal compositions with an AUC that is increased by at least 2 fold to 10 fold (or any value in between).

4 Dose Response Modulation

In a further aspect the present invention provides a process for improving the dose response of an active substance by creating cocrystals of the said active substance. Dose response is the quantitative relationship between the magnitude of response and the dose inducing the response and may be measured by conventional means known in the art. The curve relating effect (as the dependent variable) to dose (as the independent variable) for an active-cell system is the "dose-response curve". Typically, the dose-response curve is the measured response to an active substance plotted against the dose of the active substance (mg/kg) given. The dose response curve can also be a curve of AUC against the dose of the active given.

Cocrystal products of the present invention has an increased dose response curve or a more linear dose response curve than the corresponding reference compound.

5 Increased Stability

It would be highly appreciated if the present invention can provide a chance to improve the stability of an active substance by adding a cocrystal former to produce cocrystals of the active substance as compared to its pure crystalline form (e.g. free form). Such stability improvement can be expressed by the formation of less than 0.2% of any one degradant when stored at 30° C. for 2 years. The term degradant refers herein to product(s) of a single type of chemical reaction. For example, if a hydrolysis event occurs that cleaves a molecule into two products, for the purpose of the present invention, it would be considered a single degradant. Preferably less than 0.2% of any one degradant is formed when stored at 40° C. for 2 years. Alternatively, when stored at 30° C. for 3 months, less than 0.2% or 0.1% of any one degradant is formed, or when stored at 40° C. for 3 months, less than 0.2% or 0.15%, or 0.1% of any one degradant is formed. Also, when stored at 60° C. for 4 weeks, less than 0.2% or 0.1% of any one degradant is formed. The relative humidity (RH) in all cases may be specified as ambient (RH), 75% (RH), or as any single integer between 1 to 99%.

6 Difficult to Salt or Unsaltable Compounds

In a still further aspect the present invention that provides a process for making cocrystals of unsaltable or difficult to salt or form salt of active substances. Difficult to salt compounds include bases with a pKa<3 or acids with a pKa>10. Zwitter ions are also difficult to salt or considered as unsaltable compounds. It would be very much appreciated if the current invention provides the opportunity to complex the unsaltable active substances in way that it improves its physicochemical characteristics in comparison with the pure unsaltable active substance.

7 Decreasing Hygroscopicity

In a still further aspect, the present invention provides a method for decreasing the hygroscopicity of an active substance by forming a cocrystal of the said active substance. It would be useful to generate a new physical form of the active substance which is less hygroscopic than the amorphous or crystalline, free form or salt (including metal salts such as sodium, potassium, lithium, calcium, magnesium . . . etc) or another reference compound. Hygroscopicity can be assessed by dynamic vapor sorption analysis, in which 5-50 mg of the compound is suspended from a Cahn microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until equilibrium achieved. Typical equilibrium criteria include weight changes of less than 0.01% over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous above 75% RH, but below 95% RH, the experiment should be repeated with a fresh sample and the relative humidity range for the cycling should be narrowed to 5-75% RH or 10-75% RH, instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or 0.5% weight at 25 degrees C. when cycled between 10 and 75% RH (relative humidity at 25 degrees C.). The non-hygroscopic molecule, for example, should not gain or lose more than 1.0%, or 0.5% weight when cycled between 5 and 95% RH at 25 degrees C., or more than 0.25% of its weight between 10 and 75% RH. In another embodiment, a non-hygroscopic molecule will not gain or lose more than 0.25% of its weight when cycled between 5 and 95% RH.

Alternatively, for purposes of the present invention, hygroscopicity can be defined using the parameters of Callaghan et al., "Equilibrium moisture content of pharmaceutical excipients", in Api Dev. Ind. Pharm., Vol. 8, pp. 335-369 (1982). Callaghan et al. classified the degree of hygroscopicity into four classes.

Class 1: Essentially no moisture increases occur, non-hygroscopic at relative humidities below 90%.

Class 2: Essentially no moisture increases occur, slightly hygroscopic at relative humidities below 80%.

Class 3: Moisture content does not increase, more moderately hygroscopic than 5% after storage for 1 week at relative humidities below 60%.

Class 4: Moisture content increase may occur at very hygroscopic relative humidities as low as 40 to 50%.

Alternatively, for purposes of the present invention, hygroscopicity can be defined using the parameters of the European Pharmacopoeia Technical Guide (1999, p. 86) which has defined hygrospocity, based on the static method, after storage at 25 degrees C. for 24 hours at 80% RH:

Slightly hygroscopic: Increase in mass is less than 2 percent m/m and equal to or greater than 0.2 percent m/m.

Hygroscopic: Increase in mass is less than 15 percent m/m and equal to or greater than 0.2 percent m/m.

Very Hygroscopic: Increase in mass is equal to or greater than 15 percent m/m.

Deliquescent: Sufficient water is absorbed to form a liquid.

Cocrystals of the present invention can be set forth as being in Class 1, Class 2, or Class 3, or as being slightly hygroscopic, hygroscopic, or very hygroscopic. Cocrystals of the present invention can also be set forth based on their ability to reduce hygroscopicity. Thus, cocrystals of the present invention can be less hygroscopic than a reference compound. The reference compound can be specified as the active substance in free form (free acid, free base, hydrate, solvate, etc.) or salt (e.g., especially metal salts such as sodium, potassium, lithium, calcium, or magnesium). Further included in the present invention are cocrystals that do not gain or lose more than 1.0% weight at 25 degrees C. when cycled between 10 and 75% RH, wherein the reference compound gains or loses more than 1.0% weight under the same conditions. Further included in the present invention are cocrystals that do not gain or lose more than 0.5% weight at 25 degrees C. when cycled between 10 and 75% RH, wherein the reference compound gains or loses more than 0.5% or more than 1.0% weight under the same conditions. Further included in the present invention are cocrystals that do not gain or lose more than 1.0% weight at 25 degrees C. when cycled between 5 and 95% RH, wherein the reference compound gains or loses more than 1.0% weight under the same conditions. Further included in the present invention are cocrystals that do not gain or lose more than 0.5% weight at 25 degrees C. when cycled between 5 and 95% RH, wherein the reference compound gains or loses more than 0.5% or more than 1.0% weight under the same conditions. Further included in the present invention are cocrystals that do not gain or lose more than 0.25% weight at 25 degrees C. when cycled between 5 and 95% RH, wherein the reference compound gains or loses more than 0.5% or more than 1.0% weight under the same conditions.

Further included in the present invention are cocrystals that have a hygroscopicity (according to Callaghan et al.) that is at least one class lower than the reference compound or at least two classes lower than the reference compound. Included are a Class 1 cocrystal of a Class 2 reference compound, a Class 2 cocrystal of a Class 3 reference compound, a Class 3 cocrystal of a Class 4 reference compound, a Class 1 cocrystal of a Class 3 reference compound, a Class 1 cocrystal of a Class 4 reference compound, or a Class 2 cocrystal of a Class 4 reference compound.

Further included in the present invention are cocrystals that have a hygroscopicity (according to the European Pharmacopoeia Technical Guide) that is at least one class lower than the reference compound or at least two classes lower than the reference compound. Non-limiting examples include; a slightly hygroscopic cocrystal of a hygroscopic reference compound, a hygroscopic cocrystal of a very hygroscopic reference compound, a very hygroscopic cocrystal of a deliquescent reference compound, a slightly hygroscopic cocrystal of a very hygroscopic reference compound, a slightly hygroscopic cocrystal of a deliquescent reference compound, and a hygroscopic cocrystal of a deliquescent reference compound.

8 Crystallizing Amorphous Compounds

In a further aspect, the present invention provides a process for crystallizing an amorphous active substance, which process comprises:

(1) contacting in solution the active substance with a cocrystal forming compound with a SCF under supercritical fluid crystallisation conditions and removing the solvent system so as to form a cocrystal of the active substance and the cocrystal forming compound; and (2) isolating cocrystals comprising the active substance and the cocrystal forming compound.

An amorphous active substance includes compounds that do not have the capacity to form a degree of molecular order in its solid structure when crystallised by using routine methods known to workers in the field. Cocrystallisation is an interesting approach to attempt to induce or encourage molecular order in the solid phase structure by incorporating a cocrystal former that interact or complex (e.g. hydrogen bond) with the molecules of the active substance. Such molecular interaction could lead to the formation of new solid phases that have far more order in the solid structure compared with the free/pure active. It is expected that the cocrystal form of the active substance to be more stable during storage than the amorphous active substance due to the molecular order that creates a high energy barrier to break. In addition, lack of impurities in the solid phase of the cocrystal product including residual solvents from the original solution used during processing with SCFs could eliminate or dramatically reduce the solvent mediated transformation or molecular mobility of the solid phase improving thus its stability during storage. This is an added benefit to improve the performance profile of the products produced by the supercritical fluid cocrystallisation method.

9 Decreasing Form Diversity

In a still further aspect the present invention provides a process for reducing the form diversity of an active substance, where the number of forms of a cocrystal is much smaller compared to the number of forms of a reference compound (e.g. the free form or a salt of the active substance) that can be made using routine methods in the art.

10 Morphology Modulation

In a still further aspect the present invention provides a process for modifying the morphology of an active substance. In this case the interaction (e.g., H-bonding), occurs between a functional group of an active substance with a corresponding interacting group of a cocrystal former can lead into a different packing of molecules into the crystal structure compared to the pure (free form or salt) active substance and subsequently different morphology. Particle morphology can play a vital role in influencing the physicochemical characteristics (e.g. Mpt, powder flowability, compression, comminutability . . . etc) of the active substance that governs its downstream processing and final dosage form. Therefore, the current invention can provide an opportunity to improve the morphology, dosage form and ultimately performance profile of the cocrystallised active substance.

EXAMPLES

Example 1

Cocrystallisation of Carbamazepine and Acetylsalicylic Acid (Aspirin)

300 mg of carbamazepine (CBZ) was mixed with 228 mg of acetylsalicylic acid (aspirin) and dissolved in 22 ml of absolute ethanol to form the primary solution. It was then fed through a 0.075 mm diameter capillary tube at a rate of 0.3 ml/min to the SAS EM system described in FIG. 1. The distance between the tip of the capillary and the surface of the acoustic horn was 0.5 mm for all experiments of this invention. The pressure and temperature were kept constant during the experiment at 90 bar and 35° C. respectively. The flow of the $CO_2$ during the entire experiment was kept at 20 g/min as measured at the pump head. The amplitude of the acoustic horn nozzle was set at 40% and its vibration frequency at 20 kHz. At the end of experiment the solution was stopped and the vessel was flushed with copious amount of fresh $CO_2$ for 20 minutes. The system was then depressurised and the fine powder on the outlet filter collected and stored for subsequent analysis.

Figure 3:
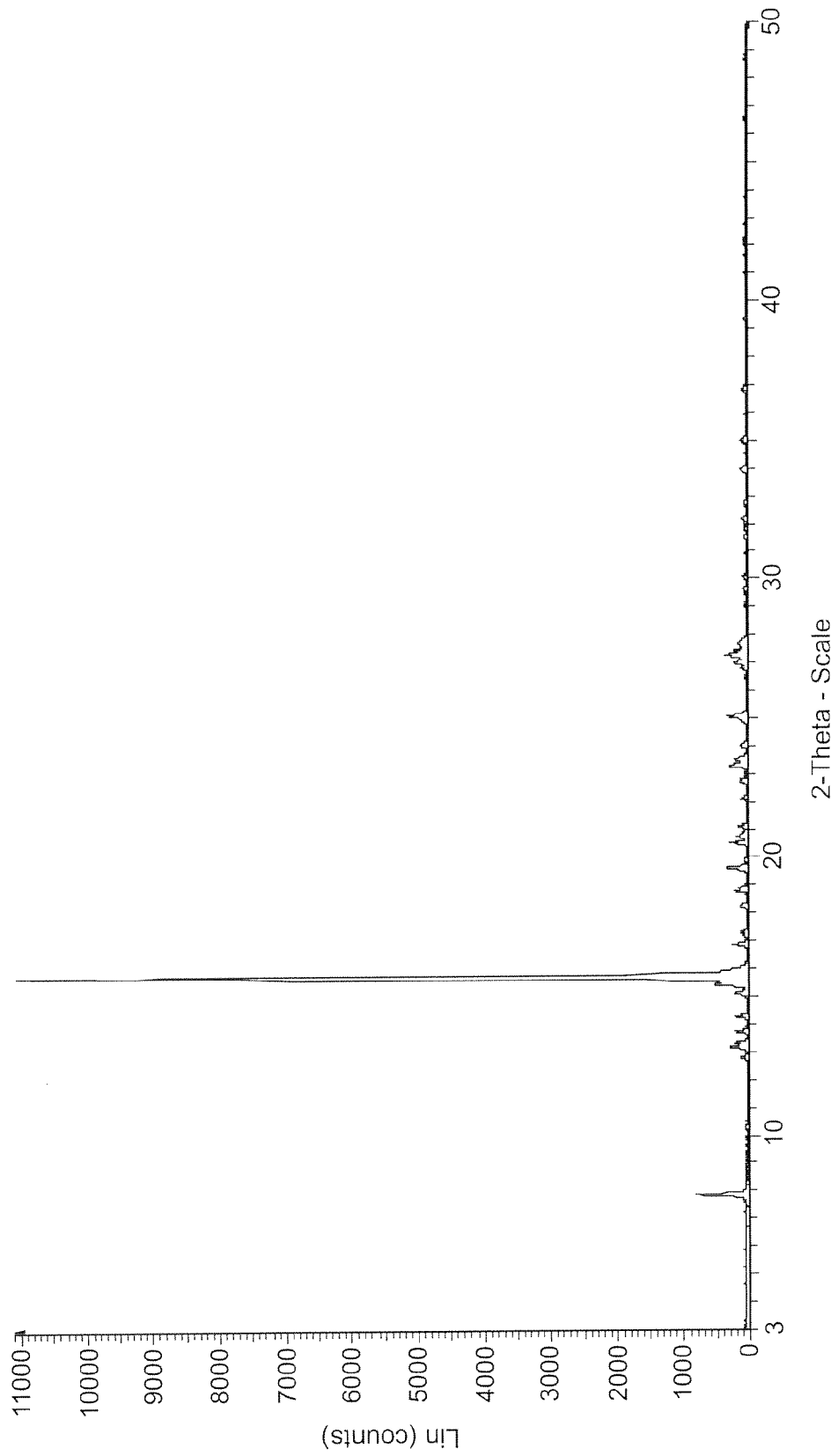
FIG. 3. PXRD pattern of 1:1 mole physical mix of CBZ-aspirin.

PXRD pattern of this sample (FIG. 2) was different from that of the physical mixture of 1:1 mole ratio of both powders (FIG. 3). In addition, DSC profiles were also different from that of the pure compounds and their physical powder mixture. This suggests that the solid phase of the SCF prepared product is different from that of the physical mix and it is more likely to be of the cocrystal of CBZ-aspirin due to the hydrogen bonding between the functional groups of both compounds that influence their molecular packing in the crystal structure and effect a new solid phase.

Figure 4:
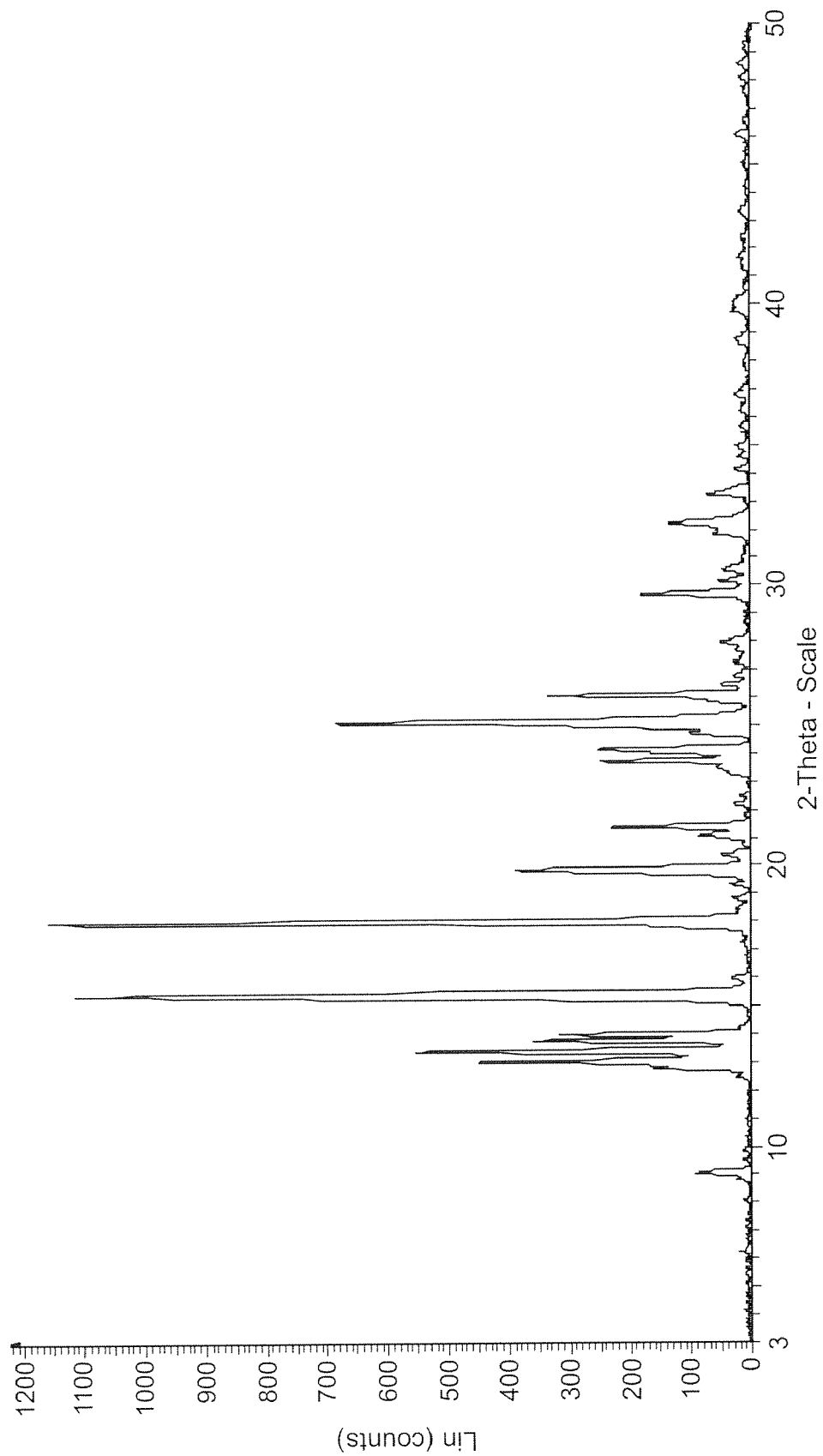
FIG. 4. PXRD pattern of CBZ-aspirin prepared at 90 bar and 60° C.

In another experiment, the temperature was raised to 60° C. while maintaining the same other working conditions above. The particulate product was analyzed by PXRD and its profile, as shown in FIG. 4 matches exactly that of the sample prepared at 35° C.

This suggests that it's possible to prepare cocrystal products of carbamazepine-acetylsalicylic acid at different $scCO_2$ conditions; gaseous-like (90 bar, 60° C.) and liquid-like (90 bar, 35° C.).

Example 2

Cocrystallisation of Carbamazepine and Saccharine

In another experiment, 294 mg of carbamazepine was mixed with 300 mg of saccharine and dissolved in 30 ml of absolute ethanol. The resulting solution was then used in the SAS EM system described in FIG. 1. The flow rate of solution and $CO_2$ measured at pump head were 0.5 ml/min and 20 g/min respectively with the pressure and temperature of the experiment at 100 bar and 40° C. respectively. The acoustic horn nozzle amplitude was 30%, and its vibration frequency 20 kHz, during solution introduction into the pressure vessel. At the end of run the solution was stopped and fresh $CO_2$ was pumped for 20 minutes to dry the cocrystallised product. The system was then depressurised and the fine particulate product collected.

Figure 5:
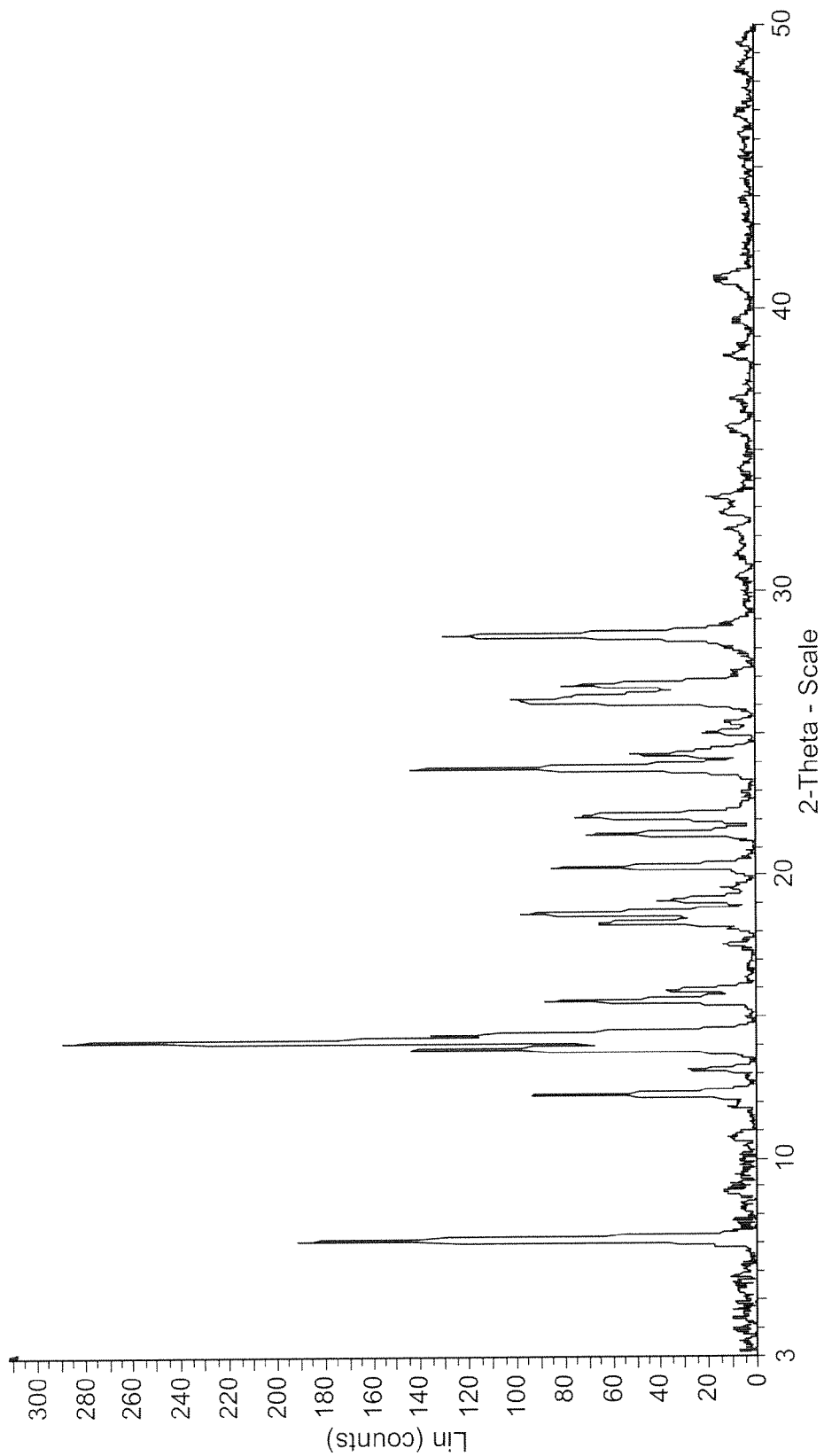
FIG. 5. PXRD pattern of CBZ-saccharine prepared at 100 bar and 40° C.

PXRD pattern of the sample (FIG. 5) clearly shows a crystalline profile.

Figure 6:
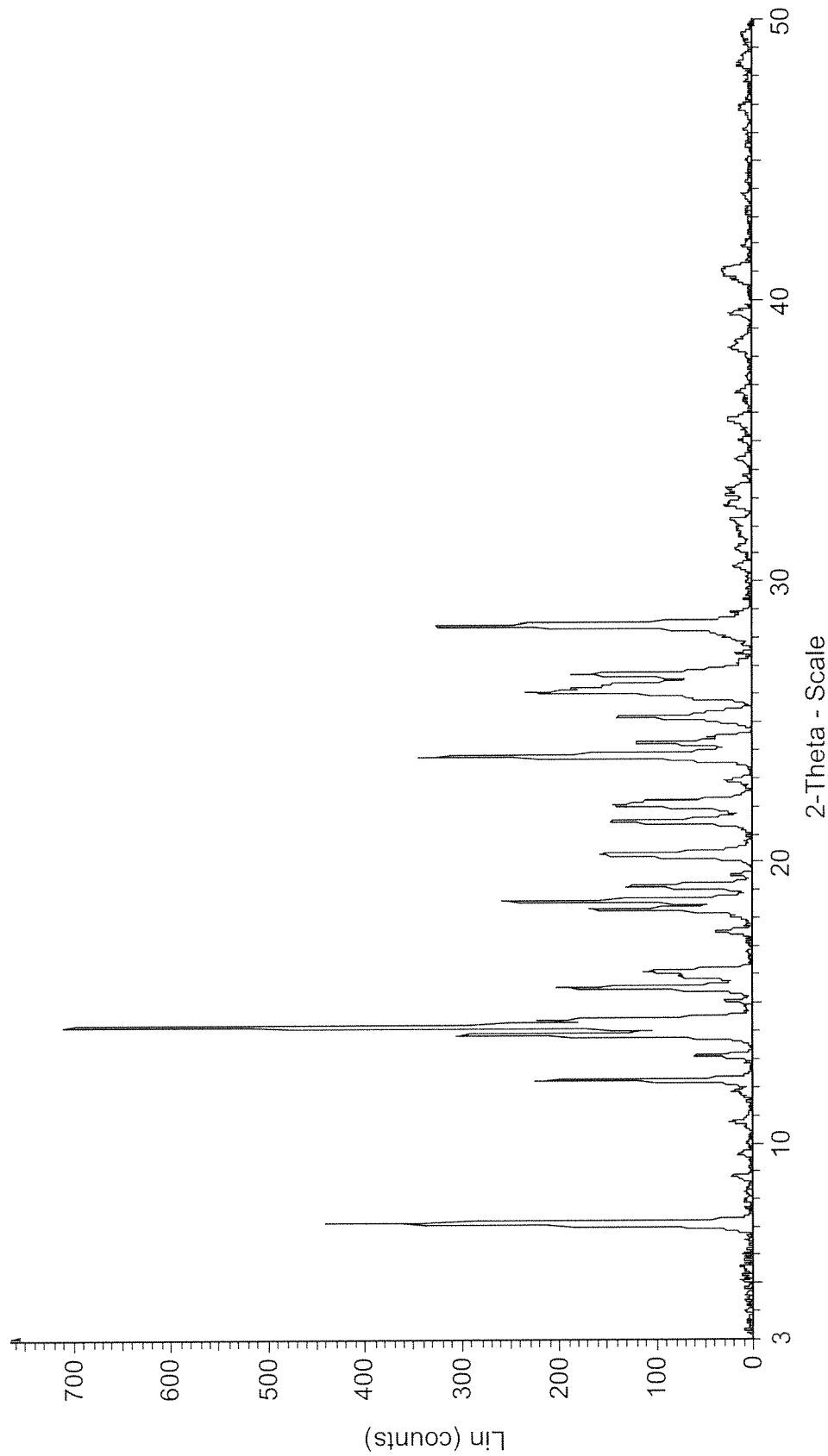
FIG. 6. PXRD pattern of CBZ-saccharine prepared at 90 bar and 60° C.
Figure 7:
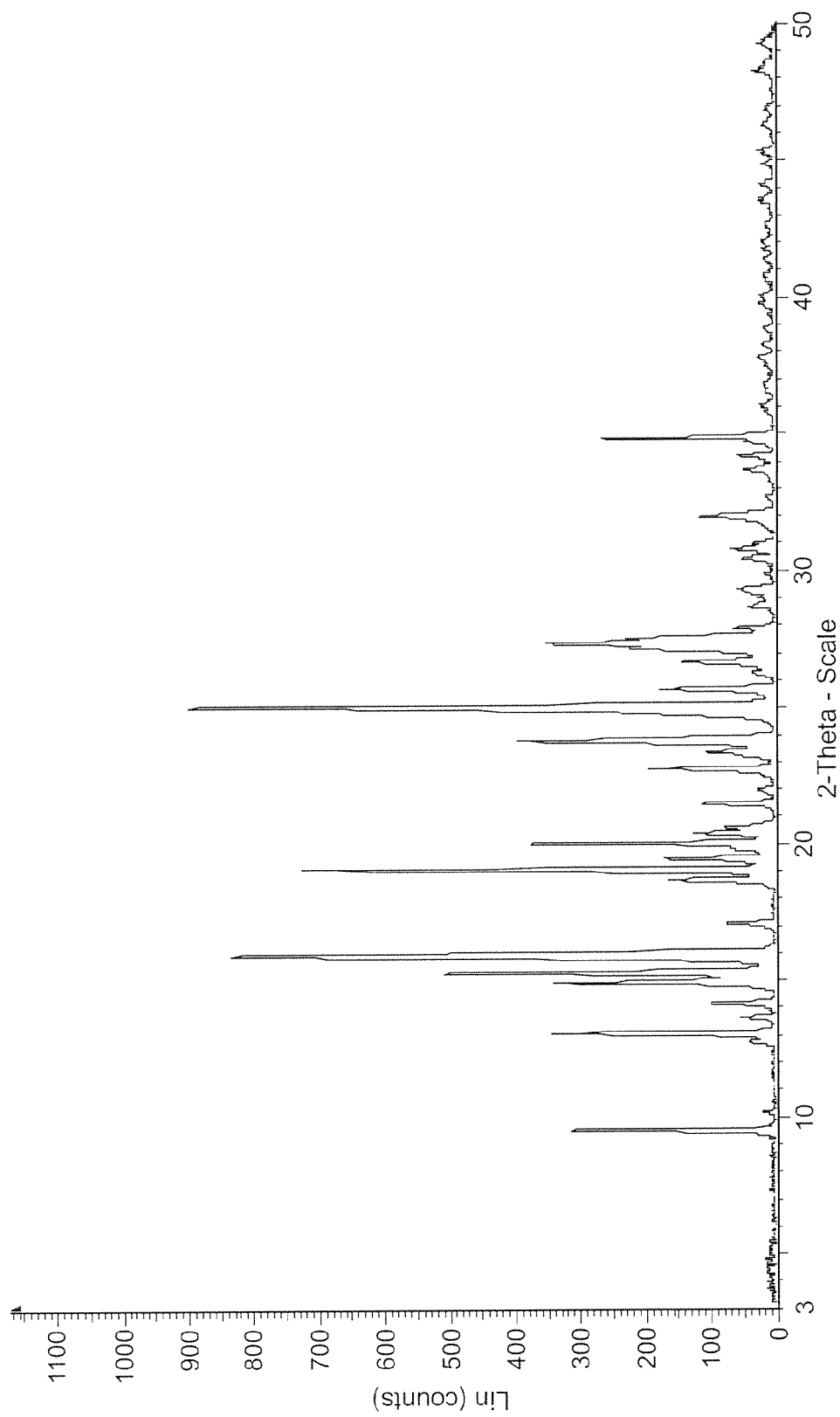
FIG. 7. PXRD pattern of CBZ-saccharine 1:1 mole, powder physical mix

In another run, the temperature was elevated to 60° C., while the pressure was reduced to 90 bar keeping all other parameters constant. A very similar profile to the previous run was obtained (see FIG. 6) suggesting that it is possible to cocrystallise carbamazepine and saccharine under different $scCO_2$ conditions. However, both PXRD patterns differ from the 1:1 mole powder physical mix (FIG. 7).

Example 3

Difficult to Cocrystallise Materials

The main reason behind selecting such materials to investigate the possibility of using SCF technology and SAS-EM to produce cocrystalline products of said materials since conventional grinding methods, solvent drop grinding and solution evaporation methods proved unsuccessful in attaining these products.

Figure 8:
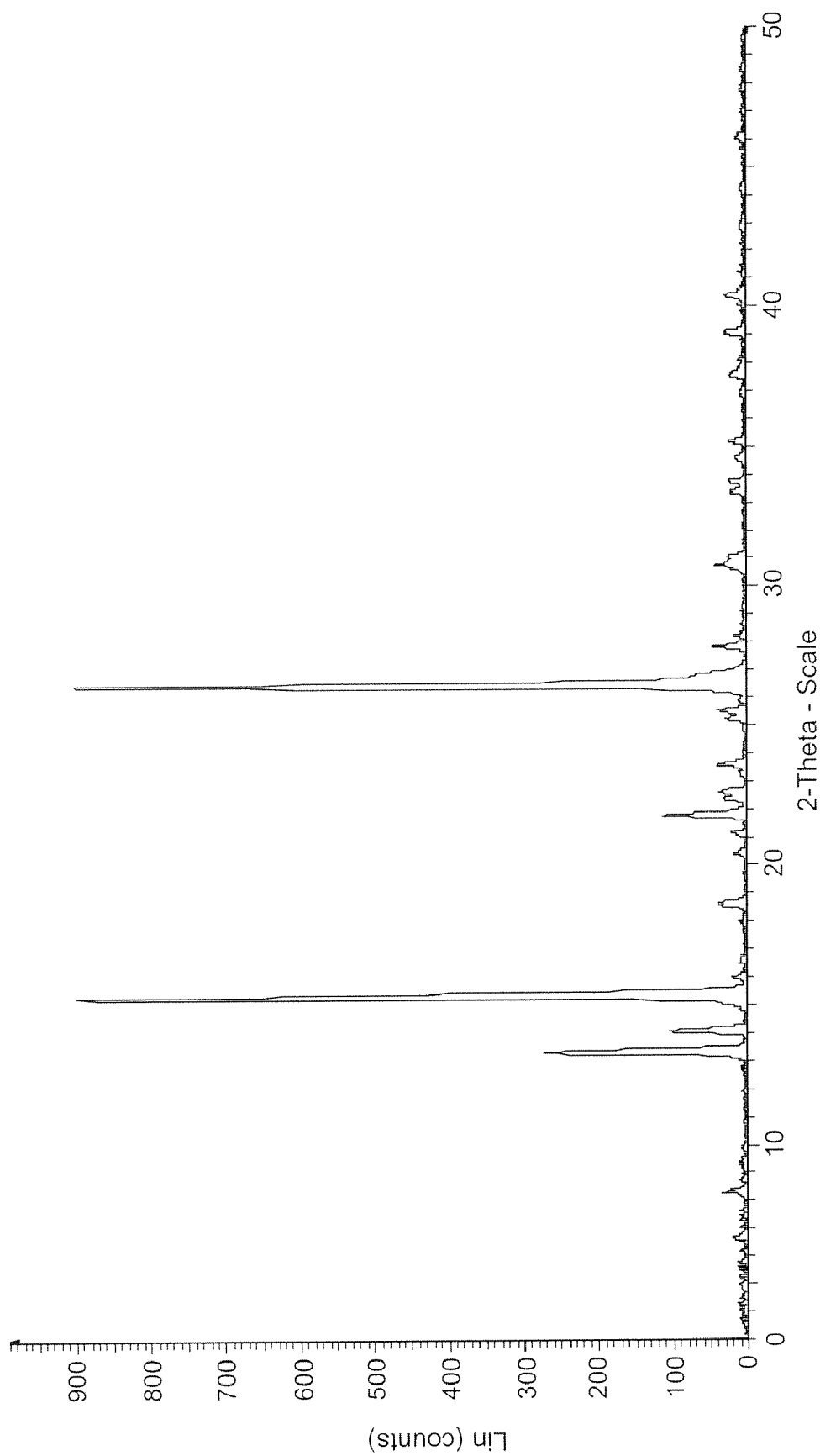
FIG. 8. PXRD pattern of phthalic anhydride and 2-methyl 4-nitroaniline prepared at 90 bar and 60° C.

150 mg of phthalic anhydride was mixed with 146 mg of 2-methyl 4-nitroaniline was mixed together and 20 ml of pure methanol was added to the mixture to form a solution. This solution was split into two 10 ml portions. One portion was then pumped at a rate of 0.2 ml/min into the SAS EM SCF crystallisation system held at 90 bar of pressure and 60° C. with $scCO_2$ flowing at 16 gm/min as measured at the pump head. The amplitude was set to 30% and the vibration frequency to 20 kHz. The fine yellow powder was collected and analyzed using PXRD. The PXRD profile suggests it is a crystalline material (FIG. 8). The second portion was left in the fume cupboard on a watch glass for several hours to allow the solvent to evaporate. After the solvent evaporation only a waxy residue was obtained that was difficult to handle or test. This suggests that the SCF is more successful in preparing difficult to cocrystallise materials than conventional solution evaporation technique.

Figure 9:
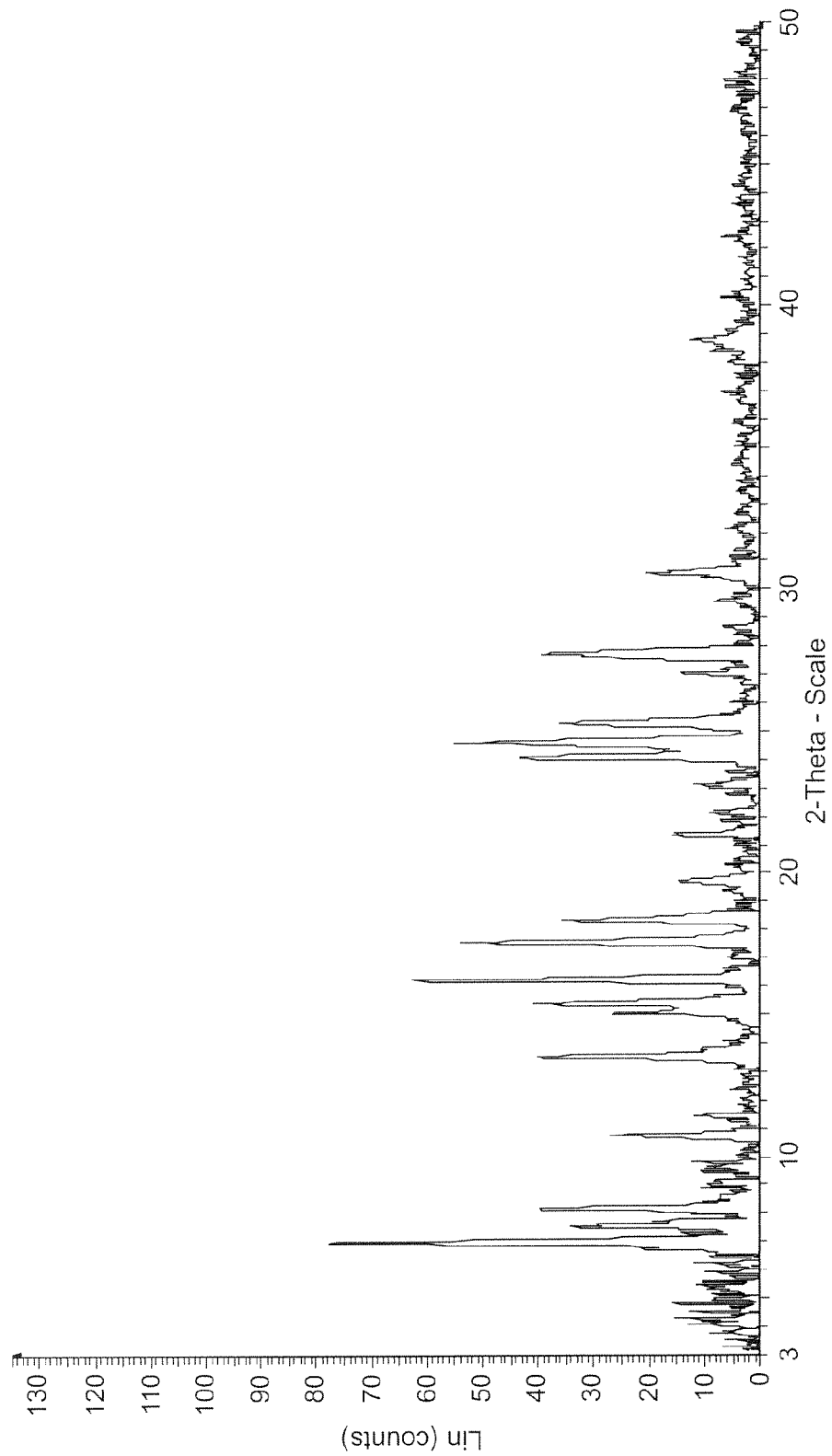
FIG. 9. PXRD pattern of phthalic anhydride-3-aminobenzoic acid prepared at 90 bar and 60° C.
Figure 10:
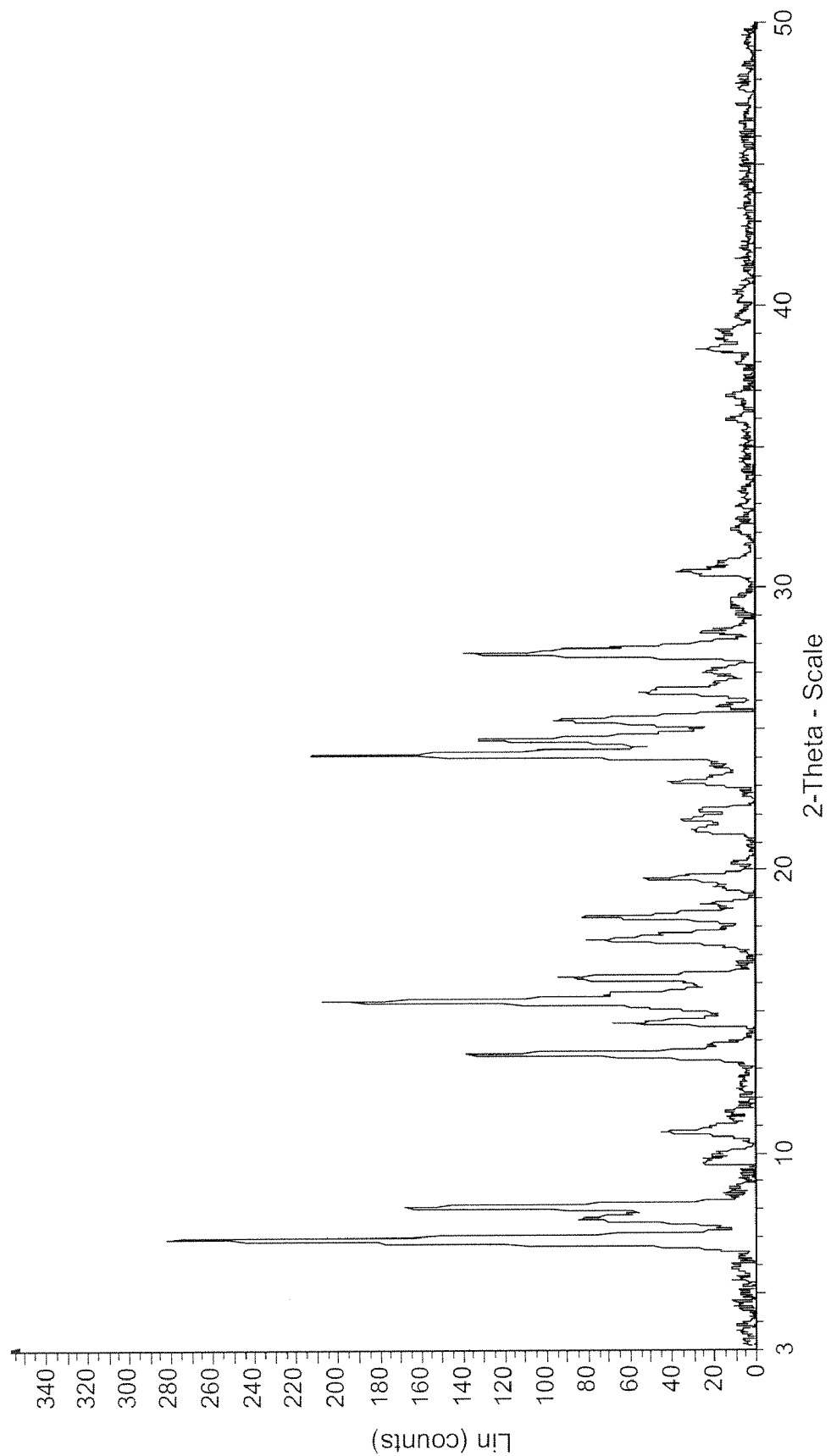
FIG. 10. PXRD pattern of phthalic anhydride and 3-aminobenzoic acid obtained by solvent evaporation.

In another set of experiments, 300 mg of phthalic anhydride was mixed with 324 mg of 3-aminobenzoic acid, 24 ml of pure methanol was added to form a solution which was split in to two 12 ml volumes. The first volume was left to evaporate in a fume hood for several hours and the dry powder collected for subsequent analysis. The second volume was fed into the SAS EM system at 0.3 ml/min with $CO_2$ flowing at a rate of 20 g/min measured at the pump head. The system pressure and temperature were kept at 90 bar and 60° C. respectively. The amplitude was 30% and the vibration frequency 20 kHz. The product collected at the end of experiment was subsequently analyzed using PXRD. The PXRD results of this particulate product shows that the profile was different from the one obtained by evaporation. The peak at (26.5°) 2-Theta scale is missing from the profile of the SCF prepared sample (FIG. 9) when compared with the solvent evaporation product (FIG. 10). It is believed that both products have different solid phase form and the SCF prepared material is a cocrystal of phthalic anhydride and 3-aminobenzoic acid rather than a physical mix of both of them.

Example 4

Difficult to Cocrystallise Materials

This Example illustrates that the process of the present invention may be used generally to cocrystallise materials which cannot be cocrystalised by conventional means or which are difficult to cocrystallise by conventional means. The same principle is equally applicable to active materials such as pharmaceutically active materials.

Figure 11:
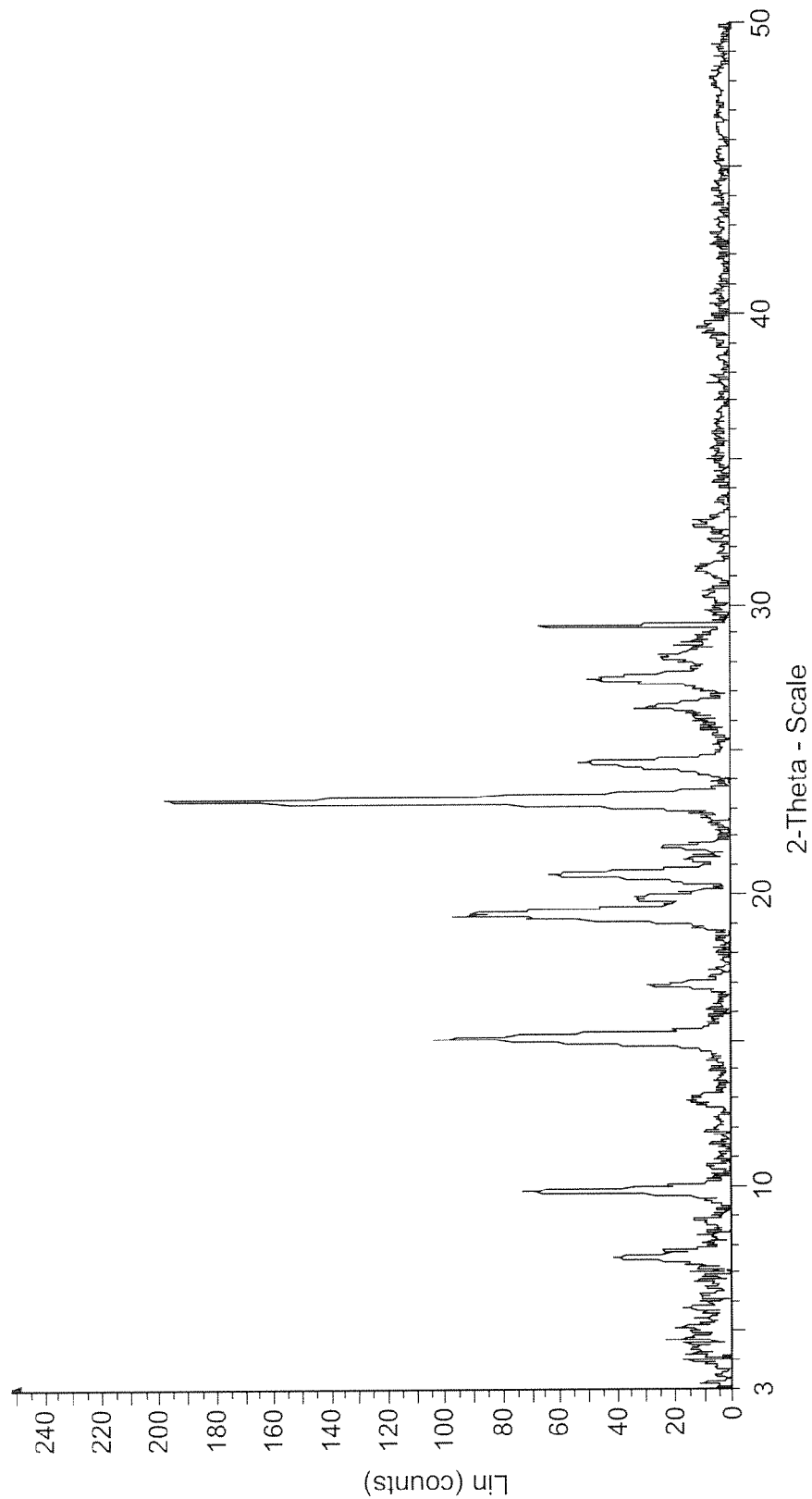
FIG. 11. PXRD pattern of phthalic anhydride-phenylene diamine prepared at 90 bar and 60° C.
Figure 12:
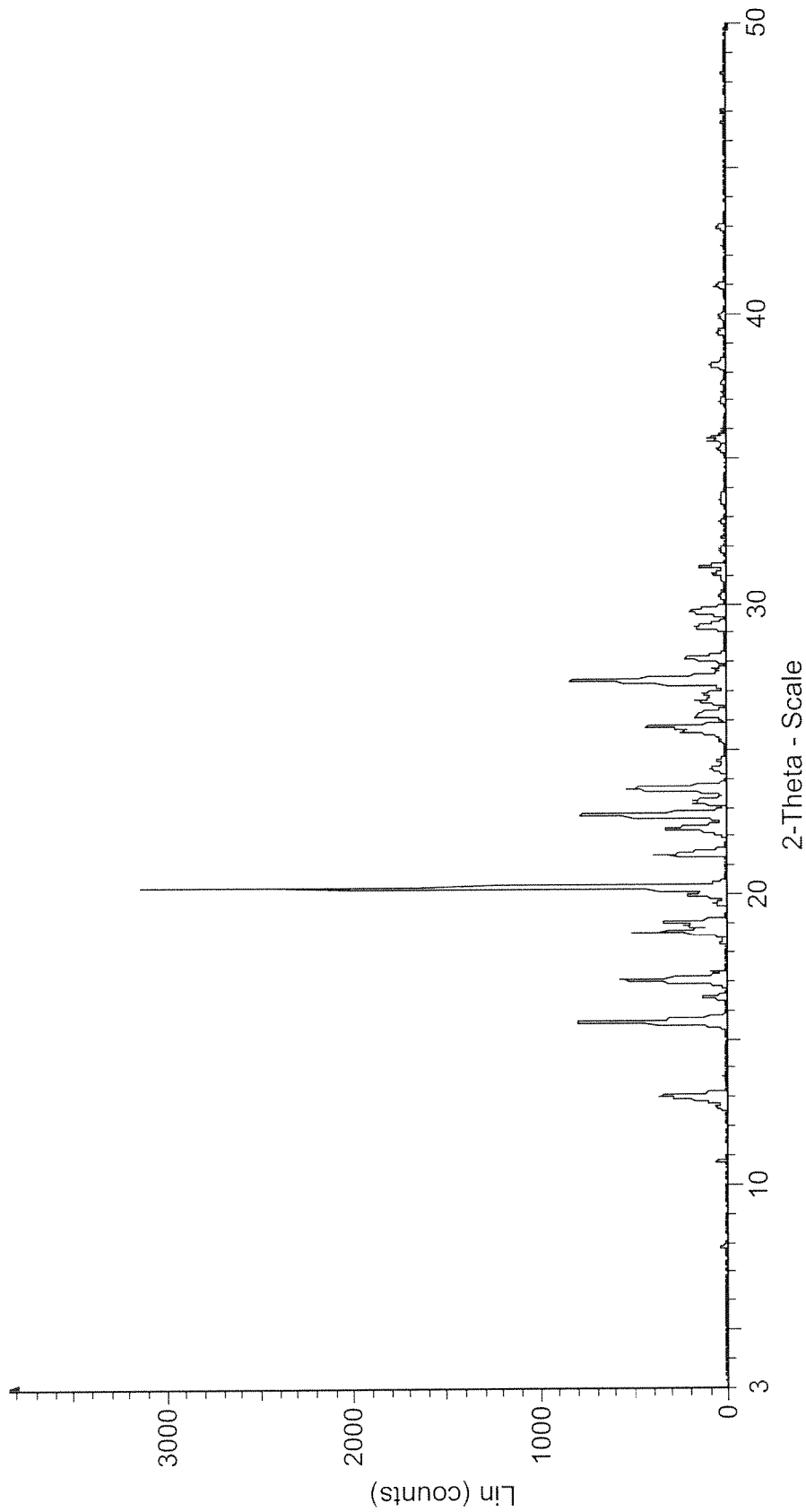
FIG. 12. PXRD pattern of phthalic anhydride-phenylene diamine physical mix.

150 mg of phthalic anhydride was dissolved 10 ml of methanol and mixed with solution of 204 mg of phenylene diamine in 1 ml of DMSO. This solution mixture was then pumped at a rate of 0.2 ml/min into the SCF crystallization SAS-EM system held at 90 bar of pressure and 60° C. with $scCO_2$ flowing at 16 gm/min as measured at the pump head. The fine grey powder was collected and analyzed using PXRD. The PXRD profile suggests it is a crystalline material (FIG. 11) and is has a different profile to that of the physical mix (FIG. 12) in which the peaks at 10° and 15° 2θ are missing and other major peaks positions has slightly shifted (for example peaks at 20.5 and 23° 2θ). This suggests that the scf prepared material has a different crystal structure to that of the physical mix and therefore a different physical entity and most likely a cocrystal.

Figure 13:
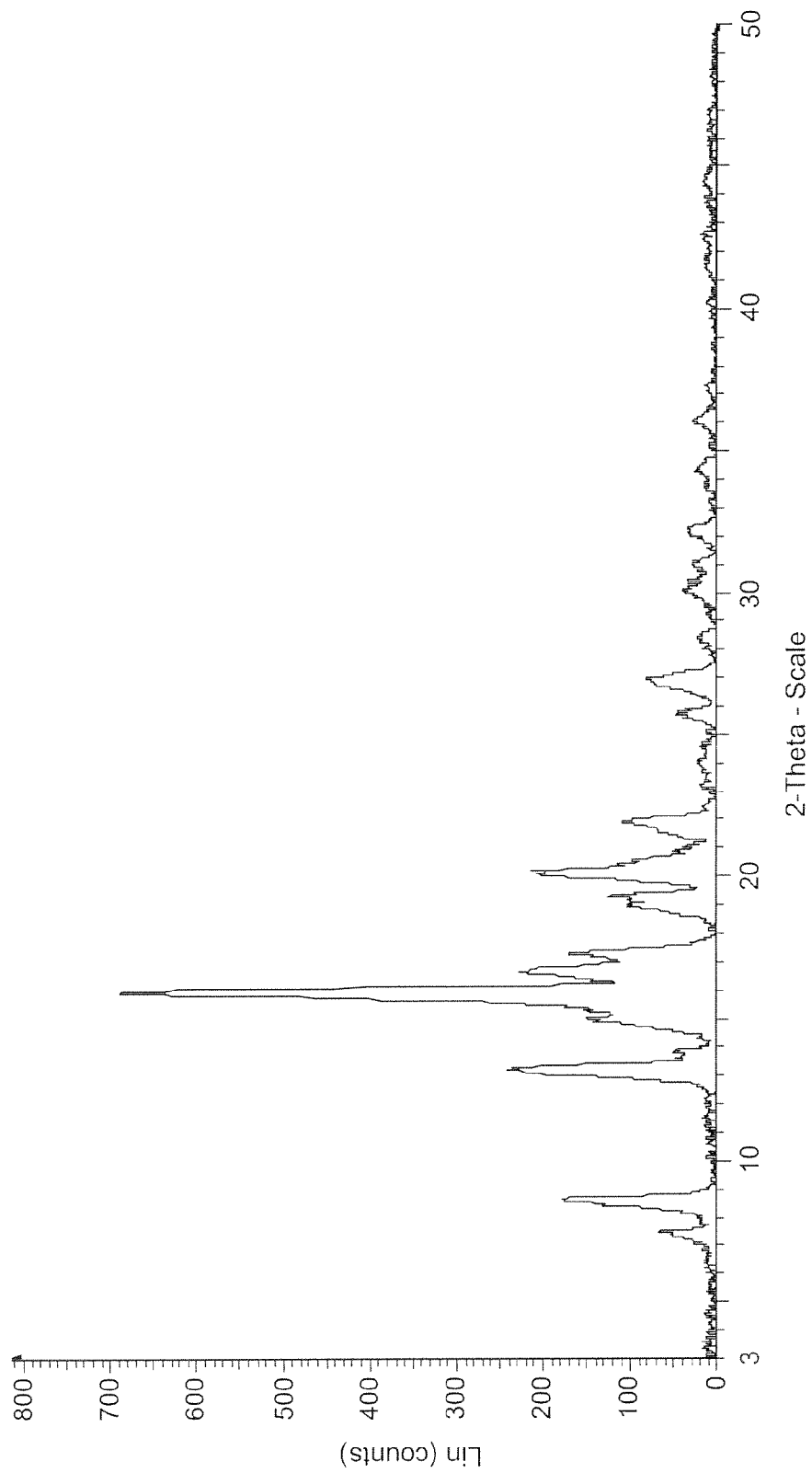
FIG. 13. PXRD pattern of phthalic anhydride-1-adamantylamine prepared at 90 bar and 60° C.
Figure 14:
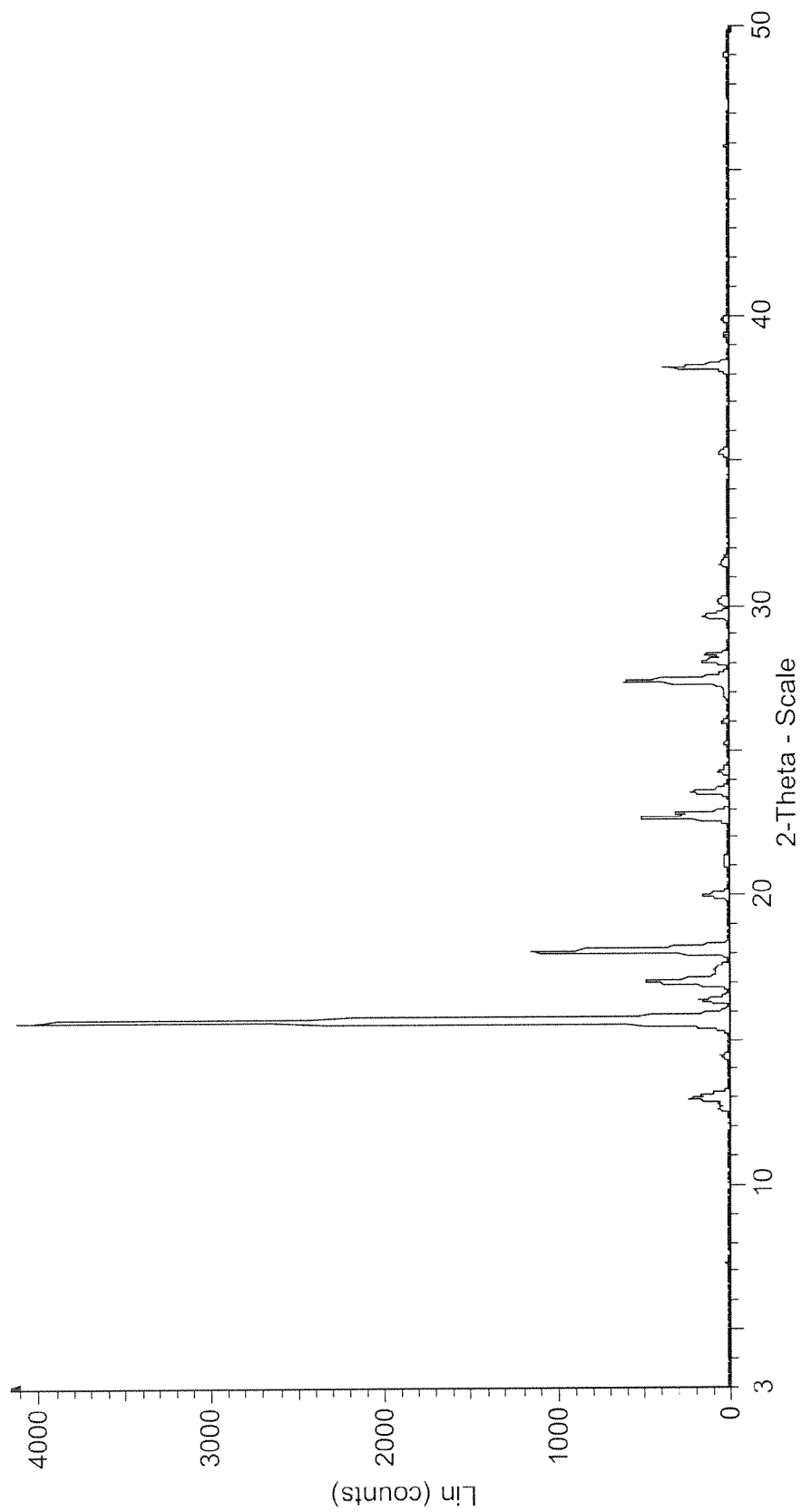
FIG. 14. PXRD pattern of phthalic anhydride-1-adamantylamine physical mix.

In another set of experiments, 148 mg of phthalic anhydride was mixed with 151 mg 1-adamantylamine and dissolved in 12 ml of pure methanol which was fed to the SCF crystallization system at 0.2 ml/min with $CO_2$ flowing at a rate of 16 g/min measured at the pump head. The system pressure and temperature were kept at 90 bar and 60° C. respectively. The fine white fluffy product collected at the end of experiment was subsequently analyzed using PXRD. The PXRD results of this particulate product (FIG. 13) shows that the profile was different from the one obtained by the physical mix. The PXRD of the physical in FIG. 14 show that major peaks of 18, 22.5, 28 and 38.5° are missing when compared to the profile in FIG. 14. In addition, peaks at 8.5 and 19° 2θ are present in FIG. 3 but missing in FIG. 14. It is believed as a result that the products have different solid phase form and the SCF prepared material is a cocrystal of phthalic anhydride and 1-adamantylamine.

Example 5

Scale-Up of Cocrystallisation by Using Seeds Prepared from SCF Technology

This Example illustrates that the process of the present invention may be used generally to cocrystallise materials which cannot be cocrystalised by conventional means or which are difficult to cocrystallise by conventional means. Such cocrystals may then be used as seed crystals for precipitation of cocrystals from solution using conventional techniques. The same principle is equally applicable to active materials such as pharmaceutically active materials.

Figure 15:
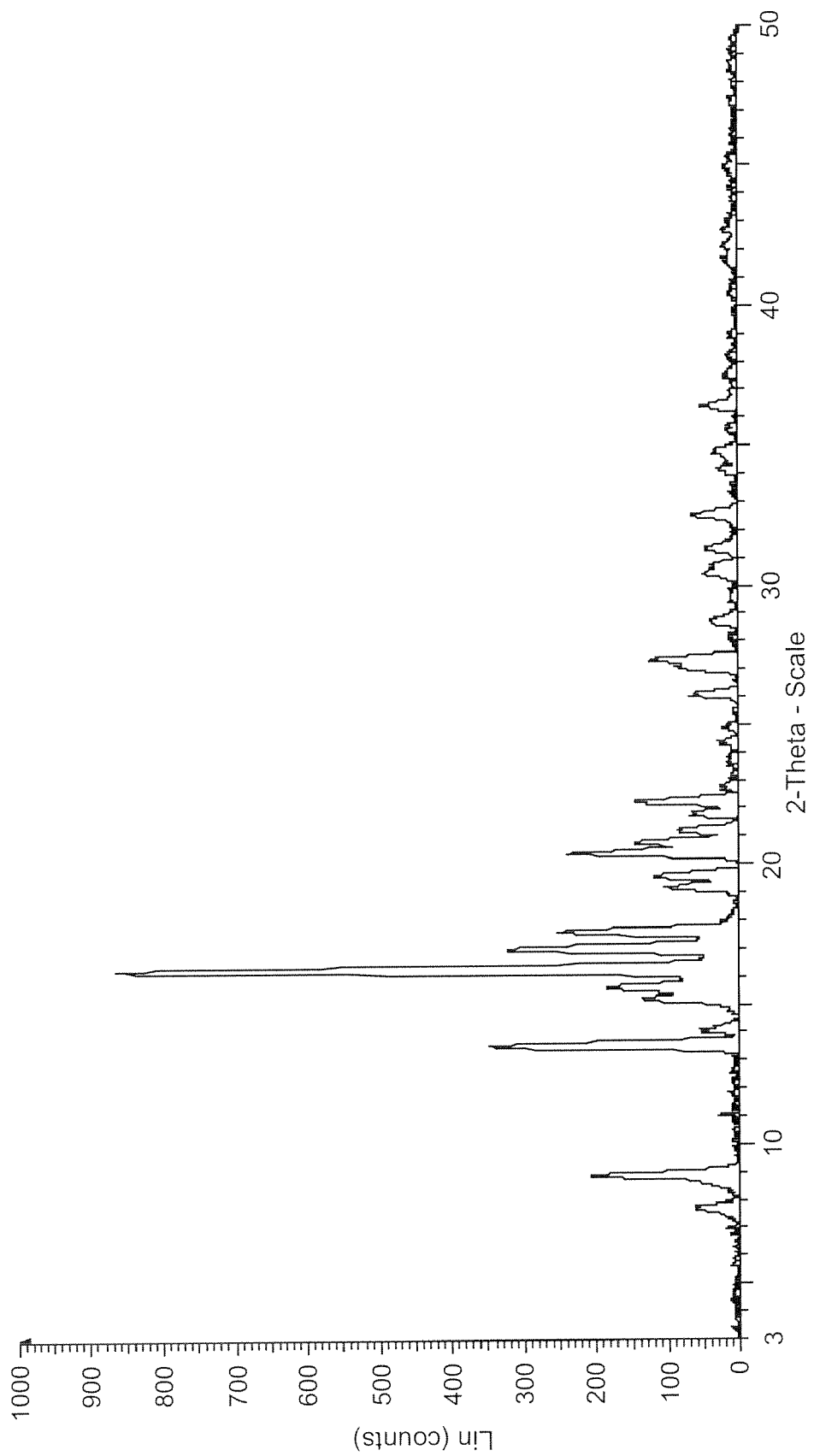
FIG. 15. PXRD pattern of phthalic anhydride-1-adamantylamine prepared using cocrystal seed material.

In another sets of experiments, 444 mg of phthalic anhydride was added to 356 mg of 1-adamantylamine, 2 ml of pure methanol was added to the solid mixture to form a solution at 20° C. 50 mg of powder of material obtained from SAS-EM SCF crystallisation of the two compounds (Phthalic anhydride and 1-adamantylamine) was added slowly to the solution until the solution become turbid and slurry start to form. The resultant solid material was dried in the oven at 25° C. and powder collected was analysed by PXRD. The PXRD profile of this product (FIG. 15) was virtually identical to that of the material prepared from SCF method (FIG. 13), where all major peaks positions are present at the same 2θ angle. Both profiles are overlapabel.

Figure 16:
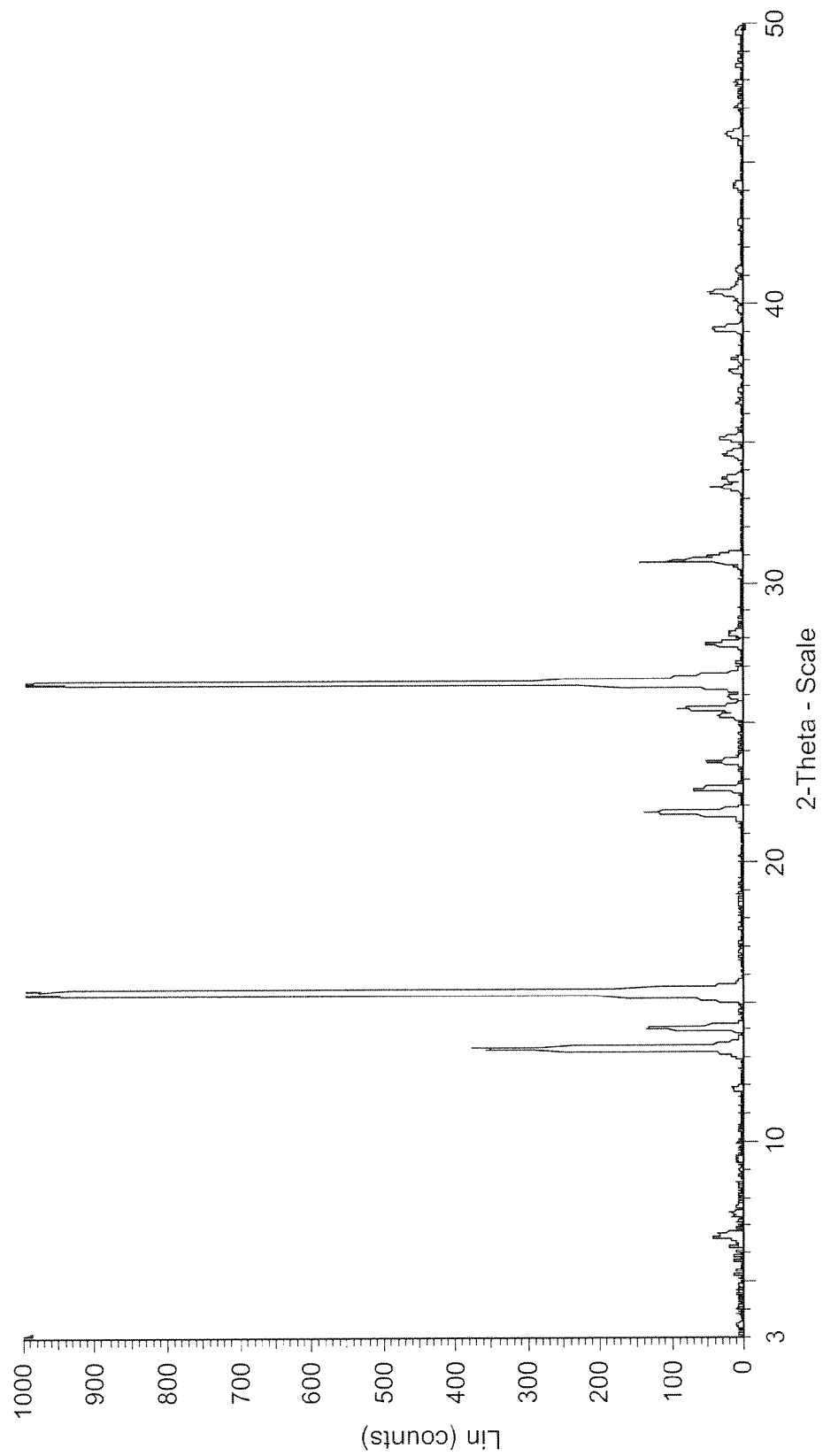
FIG. 16. PXRD pattern of phthalic anhydride and 2-methyl 4-nitroaniline prepared at 120 bar and 70° C.
Figure 17:
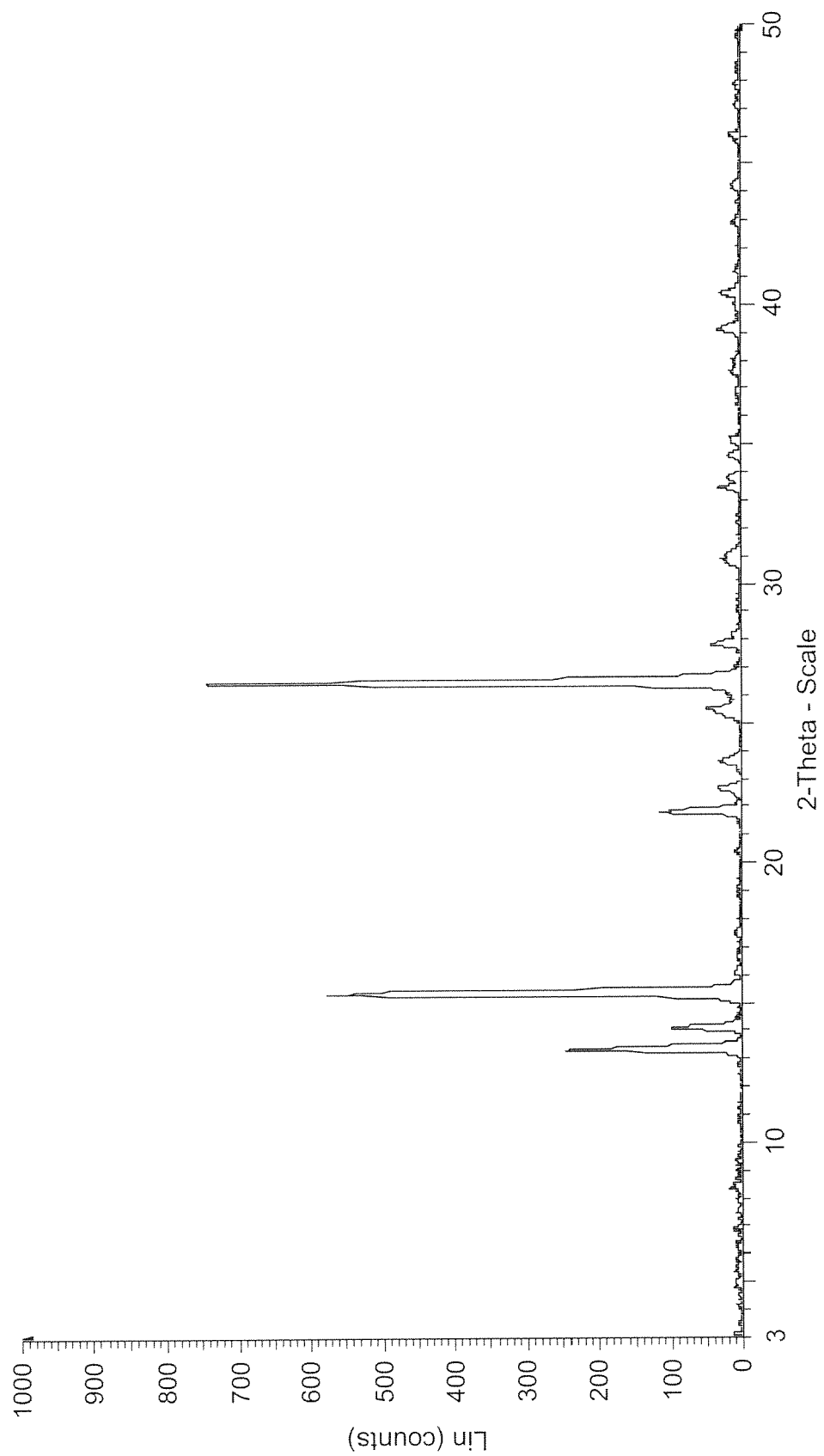
FIG. 17. PXRD pattern of phthalic anhydride and 2-methyl 4-nitroaniline prepared using cocrystal seed material.

In yet another sets of experiments, 148 mg of phthalic anhydride was mixed 152 mg of 2 methyl 4 nitroaniline and dissolved in 12 ml of pure methanol. The solution was fed to SCF SAS_EM crystallization system held at 120 bar and 70° C. at a rate 0.2 ml/min with $scCO_2$ flowing at 16 gm/min as measured at the pump head. The powder collected was analysed by PXRD (FIG. 16) which is identical to that SCF prepared at 90 bar and 60° C. (FIG. 8). A small amount of this sample was used as a seed for the following solvent crystallization experiment. 296 mg of phthalic anhydride is mixed with 304 mg of 2 methyl 4 nitroaniline, 3 ml of pure methanol was added to the mixture and heated in a water bath set at 60° C. to make a clear solution. The solution was then cooled to 5° C. 50 mg of the SCF prepared material (phtalic anhydride and 2 methyl 4 nitroaniline) was slowly added to this clear solution. During addition of the SCF prepared seeds, the solution became cloudy and white solid material precipitated at the bottom. The solid material was dried in the oven at 25° C. and the dry powder was analysed. PXRD profile (FIG. 17) of this product was near identical to that of the SCF seed material (FIG. 16). It should be noted that conventional evaporation of a solution of phthalic anhydride and 2 methyl 4 nitroaniline in pure methanol gives only a waxy residue.

These results show that it is possible to generate cocrystals of materials that are difficult to cocrystallise by conventional dry or solvent drop grinding. Such cocrystals may then be used as a seed for conventional solvent based crystallization methods for the purpose of scale up and generating large quantities of materials of interest.

The invention claimed is:

1. A process for preparing a cocrystal of an active substance and a cocrystal former, the process comprising precipitating the active substance and the cocrystal former together from solution or suspension, in the presence of a supercritical or near-critical fluid, wherein the cocrystal former is selected such that the cocrystal former and the active substance are bonded together through hydrogen bonds to form the cocrystal.

2. The process according to claim 1, wherein the supercritical or near-critical fluid is carbon dioxide.

3. The process according to claim 1, wherein the active substance and the cocrystal former are precipitated from supercritical or near-critical fluid solution or suspension by a rapid reduction in pressure.

4. The process according to claim 1, wherein the active substance and the cocrystal former are precipitated from solution or suspension by a supercritical or near-critical fluid anti-solvent.

5. The process according to claim 1, wherein the active substance and the cocrystal former are precipitated from solution or suspension using a GAS, SAS, SEDS or SAS-EM process.

6. The process according to claim 1, wherein the active substance and the cocrystal former are dissolved or suspended in a solvent system which is subsequently contacted with a supercritical or near-critical fluid and wherein the mixture of (a) the solution or suspension of the active substance and cocrystal former and (b) the supercritical or near-critical fluid is itself supercritical or near-critical.

7. The process according to claim 1, wherein the active substance and the cocrystal former are precipitated from separate solutions or suspensions.

8. The process according to claim 1, wherein the active substance is a pharmaceutically active substance.

9. The process according to claim 1, wherein the cocrystal former is selected from the group consisting of a pharmaceutically active substance and a pharmaceutically inert, pharmaceutically acceptable substance.

10. The process according to claim 1, wherein the molar ratio of the active substance to the cocrystal former is substantially stoichiometric.

11. The process according to claim 10, wherein the stoichiometric molar ratio of the active substance to the cocrystal former is selected from the group consisting of 1:1, 1:1.5, or 1:2.

12. The process according to claim 10, wherein the stoichiometric molar ratio of the active substance to the cocrystal former is 1:3.

13. The process according to claim 10, wherein the stoichiometric molar ratio of the cocrystal former to the active substance is selected from the group consisting of 1:1.5, 1:2, or 1:3.

14. The process according to claim 10, wherein the molar ratio of the active substance to the cocrystal former is within 20% of the stoichiometric value.

15. The process according to claim 14, wherein the molar ratio of the active substance to the cocrystal former is within 10% of the stoichiometric value.

16. A process for the preparation of a cocrystal of an active substance and a cocrystal former, the process comprising precipitating a cocrystal from a solution or suspension of an active substance and a cocrystal former in the presence of a cocrystal seed crystal prepared by a process according to claim 1.

17. A process for modifying a physicochemical property of an active substance, the process comprising precipitating the active substance from solution or suspension, in the presence of a supercritical or near-critical fluid, together with a cocrystal former so as to form a cocrystal precipitate having a physicochemical property different from that of the active substance, wherein the cocrystal former is selected such that the cocrystal former and the active substance are bonded together through hydrogen bonds to form the cocrystal.

18. The process according to claim 17, wherein the physicochemical property that is modified is selected from solubility, dissolution profile, bioavailability, dose response profile, stability, saltability, hygroscopicity, morphology, polymorphic form and purity and restricting polymorphic form diversity.

19. The process according to claim 17, which is used to increase the crystallinity of the active substance.

20. A process for preparing a composition containing an active substance, the process comprising forming a cocrystal comprising the active substance and a cocrystal former by precipitating the active substance and the cocrystal former together from solution or suspension, in the presence of a supercritical or near-critical fluid, wherein the cocrystal former is selected such that the cocrystal former and the active substance are bonded together through hydrogen bonds to form the cocrystal.

21. The process according to claim 20, wherein the composition is a pharmaceutical composition.

22. A cocrystal prepared using a process according to claim 1.

23. A cocrystal prepared using a process according to claim 10.

24. A cocrystal prepared using a process according to claim 16.

25. A composition containing an active substance, the composition having been prepared using a process according to claim 20.

* * * * *